(12) United States Patent
Kaufmann et al.

(10) Patent No.: US 7,605,246 B2
(45) Date of Patent: Oct. 20, 2009

(54) GENES DIFFERENTIALLY EXPRESSED IN BREAST CANCER

(75) Inventors: Joerg Kaufmann, Berlin (DE); Greg Harrowe, Berkeley, CA (US); Christoph Reinhard, Alameda, CA (US); Sanmao Kang, Richmond, CA (US)

(73) Assignee: Novartis Vaccines and Diagnostics, Inc., Emeryville, CA (US)

( * ) Notice: Subject to any disclaimer, the term of this patent is extended or adjusted under 35 U.S.C. 154(b) by 872 days.

(21) Appl. No.: 09/758,575

(22) Filed: Jan. 9, 2001

(65) Prior Publication Data

US 2002/0004239 A1    Jan. 10, 2002

Related U.S. Application Data

(60) Provisional application No. 60/175,462, filed on Jan. 10, 2000.

(51) Int. Cl.
| | |
|---|---|
| *C07H 5/00* | (2006.01) |
| *C08B 37/00* | (2006.01) |
| *C07H 19/00* | (2006.01) |
| *C07H 21/00* | (2006.01) |
| *C07H 21/02* | (2006.01) |
| *C12P 21/06* | (2006.01) |

(52) U.S. Cl. .................... 536/23.5; 536/18.7; 536/22.1; 536/23.1; 435/69.1; 530/350; 436/64; 436/86

(58) Field of Classification Search ................ 435/69.1, 435/325, 320.1, 6, 7.1; 536/23.5, 18.7, 22.1, 536/23.1; 530/300, 350; 436/64, 86
See application file for complete search history.

(56) References Cited

U.S. PATENT DOCUMENTS

2002/0081659 A1 * 6/2002 Rosen et al. ................ 435/69.1

FOREIGN PATENT DOCUMENTS

| WO | WO 93/16180 | 8/1993 |
|---|---|---|
| WO | WO 00/55320 | 9/2000 |

OTHER PUBLICATIONS

GenCore database sheets (3 sheets) Sequence alignment between US Patent Application Publication No. 2002/0081659 A1 sequence 71 versus Applicants' SEQ ID No. 1 (nucleic acid) and SEQ ID No. 2 (amino acid).*
Boehringer Mannheim Biochemicals 1991 Catalog, p. 557.*
Lazar et al. Transforming Growth Factor alpha: Mutation of Aspartic Acid 47 and Leucine 48 Results in Different Biological Activities 8(3): 1247, Mar. 1988.*
Thompson et al, "Association of Increased Basement Membrane Invasiveness With Abesence of Estrogen Receptor and Expression of Vimentin in Human Breast Cancer Cell Lines," *J. Cell Physiol.* 150(3):534-544, Mar. 1992.
Tomlinson et al., "Loss of Heterozygosity on Chromosome 11q in Breast Cancer," *J. Clin. Pathol.* 48(5):424-428, May 1995.
Winqvist et al., "Loss of Heterozygosity for Chromosome 11 in Primary Human Breast Tumors Is Associated with Poor Survival after Metastasis," *Cancer Res.* 55(12):2660-2664. Jun. 15, 1995.
Anisowicz et al., "A Novel Protease Homolog Differentially Expressed in Breast and Ovarian Cancer," *Molecular Medicine* 2(5):624-636, Sep. 1, 1996.
Database EMBL, Accession No. AC018997, Dec. 26, 1999.
Albini et al., "A Rapid in Vitro Assay for Quantitating the Invasive Potential of Tumor Cells," *Cancer Res.* 47(12):3239-3245, Jun. 15, 1987.
Bergstrom et al., "Regulatory Autonomy and Molecular Characterization of the Drosophila *out at first Gene*," *Genetics* 139(3):1331-1346, Mar. 1995.
Engel et al., "Establishment and Characterization of Three New Continuous Cell Lines Derived from Human Breast Carcinomas," *Cancer Res.* 38(10):3352-3364, Oct. 1978.
Kramer et al., "Invasion of Reconstituted Basement Membrane Matrix by Metastatic Human Tumor Cells" *Cancer Res.* 46(4 Part 2):1980-89, Apr. 1986.
Merli et al., "Promoter Specificity Mediates the Independent Regulation of Neighboring Genes," *Genes Dev.* 10(10):1260-1270, May 15, 1996.
Negrini et al., "Definition and Refinement of Chromosome 11 Regions of Loss of Heterozygosity in Breast Cancer: Identification of a New Region at 11q23.3," *Cancer Res.*55(14):3003-3007, Jul. 15, 1995.
Rishi et al., "Regulation of the *Human Retinoic Acid Receptor* α Gene in the Estrogen Receptor Negative Human Breast Carcinoma Cell Lines SKBR-3 and MDA-MB-435," *Cancer Res.* 56(22):5246-5252, Nov. 15, 1996.
Sugiura et al. "Function of α3β1-Tetraspanin Protein Complexes in Tumor Cell Invasion. Evidence for the Role of the Complexes in Production of Matrix Metalloproteinase 2 (MMP-2)," *J. Cell Biol.* 146(6):1375-1389, Sep. 20, 1999.

* cited by examiner

*Primary Examiner*—Alana M Harris
(74) *Attorney, Agent, or Firm*—Lisa Alexander; Patricia Tsao

(57) ABSTRACT

A polynucleotide sequence as shown in SEQ ID NO:1 is associated with metastatic potential of cancer cells, especially breast cancer cells. Methods are provided for determining the risk of metastasis of a tumor, by determining whether a tissue sample from a tumor expresses a polypeptide or mRNA encoded by a polynucleotide as shown in SEQ ID NO:1. Also provided are therapeutic methods and compositions.

19 Claims, 14 Drawing Sheets

SEQ ID NO:1

```
CCGCGAGGTGCGCGGTCTCTTTAAGGCGGGTCCTGGTGGTTTCTGTTTCCTGAAGGAAGTGACGGGGGGTGGGATTGAATGAAAAGTGCAAAA
CACAGGCTCGCAGCGCTGGAGCCCGGGGCCGCGGAGCCGGGCCGGGGCAGCGCCGTCTCCGCCTCGGGGCCGCCGGGGGCGCCCTGCTGAGCG
CTACCCACGTGCGTCCGCGCCACCTCGCGGGCGACCCCGCGGCCAAGGCCCCCGGCGGAGCGGCTCCCGGGCGCCCCGAACTAGCCCCCAACT
TTGGGCGAAGTTTGCCTGCGCCTCTCCCCGCCCCCACGCGGCGCGCCGGGGCCGCGGACGGCAGCGGCCCCCGGGGATGCGCCTTCCCGGGGT
ACCCCTGGCGCGCCCTGCGCTGCTGCTGCTGCCGCTGCTCGCGCCGCTGCTGGGAACGGGTGCGCCGGCCGAGCTGCGGGTCCGCGTGCG
GCTGCCGGACGGCCAGGTGACCGAGGAGAGCCTGCAGGCGGACAGCGACGCGGACAGCATCAGCCTCGAGCTGCGCAAGCCCGACGGCACCCT
CGTCTCCTTCACCGCCGACTTCAAGAAGGATGTGAAGGTCTTCCGGGCCCTGATCCTGGGGGAGCTGGAGAAGGGGCAGAGTCAGTTCCAGGC
CCTCTGCTTTGTCACCCAGCTGCAGCACAATGAGATCATCCCCAGTGAGGCCATGGCCAAGCTCCGGCAGAAAAATCCCCGGGCAGTGCGGCA
GGCGGAGGAGGTTCGGGGTCTGGAGCATCTGCACATGGATGTCGCTGTCAACTTCAGCCAGGGGGCCCTGCTGAGCCCCCATCTCCACAACGT
GTGTGCCGAGGCCGTGGATGCCATCTACACCCGCCAGGAGGATGTCCGGTTCTGGCTGGAGCAAGGTGTGGACAGTTCTGTGTTCGAGGCTCT
GCCCAAGGCCTCAGAGCAGGCGGAGCTGCCTCGCTGCAGGCAGGTGGGGGACCGCGGGAAGCCCTGCGTCTGCCACTATGGCCTGAGCCTGGC
CTGGTACCCCTGCATGCTCAAGTACTGCCACAGCCGCGACCGGCCCACGCCCTACAAGTGTGGCATCCGCAGCTGCCAGAAGAGCTACAGCTT
CGACTTCTACGTGCCCCAGAGGCAGCTGTGTCTCTGGGATGAGGATCCCTACCCAGGCTAGGGTGGGAGCAACCTGGGCGGGTGGCTGCTCTG
GGCCCACTGCTCTTCACCAGCCACTAGAGGGGGTGGCAACCCCCACCTGAGGCCTTATTTCCCTCCCTCCCCACTCCCCTGGCCCTAGAGCCT
GGGCCCCTCTGGCCCCATCTCACATGACTGTGAAGGGGGTGTGGCATGGCAGGGGGTCTCATGAAGGCACCCCCATTCCCACCCTGTGCCTTC
CTTGCGGGCAGAGAGGGAGAGAAGGGCTCCCCAGATCTACACCCCTCCCTCCTGCATCTCCCCTGGAGTGTTCACTTGCAAGCTGCCAAAACA
TGATGGCCTCTGGTTGTTCTGTTGAACTCCTTGAACGTTTAGACCCTAAAAGGAGTCTATACCTGGACACCCACCTCCCCAGACACAACTCCC
TTCCCCATGCACACATCTGGAAGGAGCTGGCCCCTCAGTCCCTTCCTACTCCCCAACAAGGGGCTCACTATCCCCAAAGAAGGAGCTGTTGGG
GACCCACGACGCAGCCCCTGTACTGGATTACAGCATATTCTCATCTCTGGCCCCGAGGCTGCCTGTGGGGCGAGTGGAGACCTCCCATCACTG
AGACAGATCACAGACCACGAGTGCCTTTCCCGGACCTGGACGTTGCCTCCAAAACAGGCACCAGCTCTTTCCCTCTCTAGACAGAAATATTTT
TGTAAGGTTCTGGGGCAGGGAGGGAGCATGAAGTACGAGGAAAACTTGAATTCCAGATTTTTAATGCAAAGTATTTATCATTTCTACCAGAAA
TAAACGTTTTAAGTTTTTACTTGACTAATGAGACCCAGAGTTTGGAGAAAACTTTTGGCCAATGCTGCCACCTGATGTCAGAAAGTGTCCCCA
CACCCTAGCAGTGGCCTATCTTGGAACAAGAACTTCGAAAGCACCTACTGTGTGCTCAGCCATTTGAGGAAGGAAGGAGGAGAAGGAAGATGT
TACTAGGGAAGGATGAGATAAAACTTCTGCACCCAAGACAATGAGACAGACATAACTGCAACCGTAGTAAGCCAGTCAGAAATAGCCAGCGCG
AAGGCAAGAGATGGGGTGGAGATTGGAACCCCGCTTCAGATCTGGGCTCGGCTACTTACCTGCTGTGCAGCCATGGGTCAAGTTGCTTGACCT
CTCTGTGCCTCCACTCCCTTAGCTATAAATGAGCTTACTT
```

Fig. 1

SEQ ID NO:2

MRLPGVPLARPALLLLLPLLAPLLGTGAPAELRVRVRLPDGQVTEESLQADSDADSISLELRKPDGTLVSFTADFKKDVKVFRALILGELEKG
QSQFQALCFVTQLQHNEIIPSEAMAKLRQKNPRAVRQAEEVRGLEHLHMDVAVNFSQGALLSPHLHNVCAEAVDAIYTRQEDVRFWLEQGVDS
SVFEALPKASEQAELPRCRQVGDRGKPCVCHYGLSLAWYPCMLKYCHSRDRPTPYKCGIRSCQKSYSFDFYVPQRQLCLWDEDPYPG*

Fig. 2

SEQ ID NO:3

MRLPGVPLARPALLLLLPLLAPLLG TGAPA

Fig. 3

Sequence Range: 1 to 2366

```
                   10        20        30        40        50        60        70        80        90
SEQ ID NO:1  CCGCGAGGTGCGCGGTCTCTTTAAGGCGGGTCCTGGTGGTTTCTGTTTCCTGAAGGAAGTGACGGGGGGTGGGATTGAATGAAAAGTGCA
             GGCGCTCCACGCGCCAGAGAAATTCCGCCCAGGACCACCAAAGACAAAGGACTTCCTTCACTGCCCCCCACCCTAACTTACTTTTCACGT
                  100       110       120       130       140       150       160       170       180
             AAACACAGGCTCGCAGCGCTGGAGCCCGGGGCCGCGGAGCCGGGCCGGGGCAGCGCCGTCTCCGCCTCGGGGCCGCCGGGGGCGCCCTGC
             TTTGTGTCCGAGCGTCGCGACCTCGGGCCCCGGCGCCTCGGCCCGGCCCCGTCGCGGCAGAGGCGGAGCCCCGGCGGCCCCCGCGGGACG
                  190       200       210       220       230       240       250       260       270
             TGAGCGCTACCCACGTGCGTCCGCGCCACCTCGCGGGCGACCCCGCGGCCAAGGCCCCCGGCGGAGCGGCTCCCGGGCGCCCCGAACTAG
             ACTCGCGATGGGTGCACGCAGGCGCGGTGGAGCGCCCGCTGGGGCGCCGGTTCCGGGGGCCGCCTCGCCGAGGGCCCGCGGGGCTTGATC 280       290       300       310       320       330       340       350       360
             CCCCCAACTTTGGGCGAAGTTTGCCTGCGCCTCTCCCCGCCCCCACGCGGCGCGCCGGGGCCGCGGACGGCAGCGGCCCCCGGGGATGCG
             GGGGGTTGAAACCCGCTTCAAACGGACGCGGAGAGGGGCGGGGGTGCGCCGCGCGGCCCCGGCGCCTGCCGTCGCCGGGGGCCCCTACGC
SEQ ID NO:2       M  R>
                                      _____TRANSLATION OF OAFHUMAN [A]                        >

370       380       390       400       410       420       430       440       450
             CCTTCCCGGGGTACCCCTGGCGCGCCCTGCGCTGCTGCTGCTGCTGCCGCTGCTCGCGCCGCTGCTGGGAACGGGTGCGCCGGCCGAGCT
             GGAAGGGCCCCATGGGGACCGCGCGGGACGCGACGACGACGACGACGGCGACGAGCGCGGCGACGACCCTTGCCCACGCGGCCGGCTCGA
              L  P  G  V  P  L  A  R  P  A  L  L  L  L  L  P  L  L  A  P  L  L  G  T  G  A  P  A  E  L>
                                      _____TRANSLATION OF OAFHUMAN [A]                        >

460       470       480       490       500       510       520       530       540
             GCGGGTCCGCGTGCGGCTGCCGGACAGGCCAGGTGACCGAGGAGAGCCTGCAGGCGGACAGCGACGCGGACAGCATCAGCCTCGAGCTGCG
             CGCCCAGGCGCACGCCGACGGCCTGCCGGTCCACTGGCTCCTCTCGGACGTCCGCCTGTCGCTGCGCCTGTCGTAGTCGGAGCTCGACGC
              R  V  R  V  R  L  P  D  G  Q  V  T  E  E  S  L  Q  A  D  S  D  A  D  S  I  S  L  E  L  R>
                                      _____TRANSLATION OF OAFHUMAN [A]                        >

550       560       570       580       590       600       610       620       630
             CAAGCCCGACGGCACCCTCGTCTCCTTCACCGCCGACTTCAAGAAGGATGTGAAGGTCTTCCGGGCCCTGATCCTGGGGGAGCTGGAGAA
             GTTCGGGCTGCCGTGGGAGCAGAGGAAGTGGCGGCTGAAGTTCTTCCTACACTTCCAGAAGGCCCGGGACTAGGACCCCCTCGACCTCTT
              K  P  D  G  T  L  V  S  F  T  A  D  F  K  K  D  V  K  V  F  R  A  L  I  L  G  E  L  E  K>
                                      _____TRANSLATION OF OAFHUMAN [A]                        >

640       650       660       670       680       690       700       710       720
             GGGGCAGAGTCAGTTCCAGGCCCTCTGCTTTGTCACCCAGCTGCAGCACAATGAGATCATCCCCAGTGAGGCCATGGCCAAGCTCCGGCA
             CCCCGTCTCAGTCAAGGTCCGGGAGACGAAACAGTGGGTCGACGTCGTGTTACTCTAGTAGGGGTCACTCCGGTACCGGTTCGAGGCCGT
              G  Q  S  Q  F  Q  A  L  C  F  V  T  Q  L  Q  H  N  E  I  I  P  S  E  A  M  A  K  L  R  Q>
                                      _____TRANSLATION OF OAFHUMAN [A]                        >
```

*Fig. 4A*

```
        730       740       750       760       770       780       790       800       810
GAAAAATCCCCGGGCAGTGCGGCAGGCGGAGGAGGTTCGGGGTCTGGAGCATCTGCACATGGATGTCGCTGTCAACTTCAGCCAGGGGGC
CTTTTTAGGGGCCCGTCACGCCGTCCGCCTCCTCCAAGCCCCAGACCTCGTAGACGTGTACCTACAGCGACAGTTGAAGTCGGTCCCCCG
  K  N  P  R  A  V  R  Q  A  E  E  V  R  G  L  E  H  L  H  M  D  V  A  V  N  F  S  Q  G  A>
                              TRANSLATION OF OAFHUMAN [A]                                  >

820       830       840       850       860       870       880       890       900
CCTGCTGAGCCCCCATCTCCACAACGTGTGTGCCGAGGCCGTGGATGCCATCTACACCCGCCAGGAGGATGTCCGGTTCTGGCTGGAGCA
GGACGACTCGGGGGTAGAGGTGTTGCACACACGGCTCCGGCACCTACGGTAGATGTGGGCGGTCCTCCTACAGGCCAAGACCGACCTCGT
  L  L  S  P  H  L  H  N  V  C  A  E  A  V  D  A  I  Y  T  R  Q  E  D  V  R  F  W  L  E  Q>
                              TRANSLATION OF OAFHUMAN [A]                                  >

910       920       930       940       950       960       970       980       990
AGGTGTGGACAGTTCTGTGTTCGAGGCTCTGCCCAAGGCCTCAGAGCAGGCGGAGCTGCCTCGCTGCAGGCAGGTGGGGGACCGCGGGAA
TCCACACCTGTCAAGACACAAGCTCCGAGACGGGTTCCGGAGTCTCGTCCGCCTCGACGGAGCGACGTCCGTCCACCCCCTGGCGCCCTT
  G  V  D  S  S  V  F  E  A  L  P  K  A  S  E  Q  A  E  L  P  R  C  R  Q  V  G  D  R  G  K>
                              TRANSLATION OF OAFHUMAN [A]                                  >

1000      1010      1020      1030      1040      1050      1060      1070      1080
GCCCTGCGTCTGCCACTATGGCCTGAGCCTGGCCTGGTACCCCTGCATGCTCAAGTACTGCCACAGCCGCGACCGGCCCACGCCCTACAA
CGGGACGCAGACGGTGATACCGGACTCGGACCGGACCATGGGGACGTACGAGTTCATGACGGTGTCGGCGCTGGCCGGGTGCGGGATGTT
  P  C  V  C  H  Y  G  L  S  L  A  W  Y  P  C  M  L  K  Y  C  H  S  R  D  R  P  T  P  Y  K>
                              TRANSLATION OF OAFHUMAN [A]                                  >

1090      1100      1110      1120      1130      1140      1150      1160      1170
GTGTGGCATCCGCAGCTGCCAGAAGAGCTACAGCTTCGACTTCTACGTGCCCCAGAGGCAGCTGTGTCTCTGGGATGAGGATCCCTACCC
CACACCGTAGGCGTCGACGGTCTTCTCGATGTCGAAGCTGAAGATGCACGGGGTCTCCGTCGACACAGAGACCCTACTCCTAGGGATGGG
  C  G  I  R  S  C  Q  K  S  Y  S  F  D  F  Y  V  P  Q  R  Q  L  C  L  W  D  E  D  P  Y  P>
                              TRANSLATION OF OAFHUMAN [A]                                  >

1180      1190      1200      1210      1220      1230      1240      1250      1260
AGGCTAGGGTGGGAGCAACCTGGGCGGGTGGCTGCTCTGGGCCCACTGCTCTTCACCAGCCACTAGAGGGGGTGGCAACCCCCACCTGAG
TCCGATCCCACCCTCGTTGGACCCGCCCACCGACGAGACCCGGGTGACGAGAAGTGGTCGGTGATCTCCCCCACCGTTGGGGGTGGACTC
  G  *

1270      1280      1290      1300      1310      1320      1330      1340      1350
GCCTTATTTCCCTCCCTCCCCACTCCCCTGGCCCTAGAGCCTGGGCCCCTCTGGCCCCATCTCACATGACTGTGAAGGGGGTGTGGCATG
CGGAATAAAGGGAGGGAGGGGTGAGGGGACCGGGATCTCGGACCCGGGGAGACCGGGGTAGAGTGTACTGACACTTCCCCCACACCGTAC
```

*Fig. 4B*

```
       1360      1370      1380      1390      1400      1410      1420      1430      1440
GCAGGGGGTCTCATGAAGGCACCCCCATTCCCACCCTGTGCCTTCCTTGCGGGCAGAGAGGGAGAGAAGGGCTCCCCAGATCTACACCCC
CGTCCCCCAGAGTACTTCCGTGGGGGTAAGGGTGGGACACGGAAGGAACGCCCGTCTCTCCCTCTCTTCCCGAGGGGTCTAGATGTGGGG 1450      1460      1470      1480      1490      1500      1510      1520      1530
TCCCTCCTGCATCTCCCCTGGAGTGTTCACTTGCAAGCTGCCAAAACATGATGGCCTCTGGTTGTTCTGTTGAACTCCTTGAACGTTTAG
AGGGAGGACGTAGAGGGGACCTCACAAGTGAACGTTCGACGGTTTTGTACTACCGGAGACCAACAAGACAACTTGAGGAACTTGCAAATC 1540      1550      1560      1570      1580      1590      1600      1610      1620
ACCCTAAAAGGAGTCTATACCTGGACACCCACCTCCCCAGACACAACTCCCTTCCCCATGCACACATCTGGAAGGAGCTGGCCCCTCAGT
TGGGATTTTCCTCAGATATGGACCTGTGGGTGGAGGGGTCTGTGTTGAGGGAAGGGGTACGTGTGTAGACCTTCCTCGACCGGGGAGTCA 1630      1640      1650      1660      1670      1680      1690      1700      1710
CCCTTCCTACTCCCCAACAAGGGGCTCACTATCCCCAAAGAAGGAGCTGTTGGGGACCCACGACGCAGCCCCTGTACTGGATTACAGCAT
GGGAAGGATGAGGGGTTGTTCCCCGAGTGATAGGGGTTTCTTCCTCGACAACCCCTGGGTGCTGCGTCGGGACATGACCTAATGTCGTA 1720      1730      1740      1750      1760      1770      1780      1790      1800
ATTCTCATCTCTGGCCCCGAGGCTGCCTGTGGGGCGAGTGGAGACCTCCCATCACTGAGACAGATCACAGACCACGAGTGCCTTTCCCGG
TAAGAGTAGAGACCGGGGCTCCGACGGACACCCCGCTCACCTCTGGAGGGTAGTGACTCTGTCTAGTGTCTGGTGCTCACGGAAAGGGCC 1810      1820      1830      1840      1850      1860      1870      1880      1890
ACCTGGACGTTGCCTCCAAAACAGGCACCAGCTCTTTCCCTCTCTAGACAGAAATATTTTTGTAAGGTTCTGGGGCAGGGAGGGAGCATG
TGGACCTGCAACGGAGGTTTTGTCCGTGGTCGAGAAAGGGAGAGATCTGTCTTTATAAAAACATTCCAAGACCCCGTCCCTCCCTCGTAC 1900      1910      1920      1930      1940      1950      1960      1970      1980
AAGTACGAGGAAAACTTGAATTCCAGATTTTTAATGCAAAGTATTTATCATTTCTACCAGAAATAAACGTTTTAAGTTTTTACTTGACTA
TTCATGCTCCTTTTGAACTTAAGGTCTAAAAATTACGTTTCATAAATAGTAAAGATGGTCTTTATTTGCAAAATTCAAAAATGAACTGAT 1990      2000      2010      2020      2030      2040      2050      2060      2070
ATGAGACCCAGAGTTTGGAGAAAACTTTTGGCCAATGCTGCCACCTGATGTCAGAAAGTGTCCCCACACCCTAGCAGTGGCCTATCTTGG
TACTCTGGGTCTCAAACCTCTTTTGAAAACCGGTTACGACGGTGGACTACAGTCTTTCACAGGGGTGTGGGATCGTCACCGGATAGAACC 2080      2090      2100      2110      2120      2130      2140      2150      2160
AACAAGAACTTCGAAAGCACCTACTGTGTGCTCAGCCATTTGAGGAAGGAAGGAGGAGAAGGAAGATGTTACTAGGGAAGGATGAGATAA
TTGTTCTTGAAGCTTTCGTGGATGACACACGAGTCGGTAAACTCCTTCCTTCCTCCTCTTCCTTCTACAATGATCCCTTCCTACTCTATT
```

*Fig. 4C*

```
         2170      2180      2190      2200      2210      2220      2230      2240      2250
AACTTCTGCACCCAAGACAATGAGACAGACATAACTGCAACCGTAGTAAGCCAGTCAGAAATAGCCAGCGCGAAGGCAAGAGATGGGGTG
TTGAAGACGTGGGTTCTGTTACTCTGTCTGTATTGACGTTGGCATCATTCGGTCAGTCTTTATCGGTCGCGCTTCCGTTCTCTACCCCAC 2260      2270      2280      2290      2300      2310      2320      2330      2340
GAGATTGGAACCCCGCTTCAGATCTGGGCTCGGCTACTTACCTGCTGTGCAGCCATGGGTCAAGTTGCTTGACCTCTCTGTGCCTCCACT
CTCTAACCTTGGGGCGAAGTCTAGACCCGAGCCGATGAATGGACGACACGTCGGTACCCAGTTCAACGAACTGGAGAGACACGGAGGTGA
         2350      2360
CCCTTAGCTATAAAATGAGCTTACTT
GGGAATCGATATTTTACTCGAATGAA
```

*Fig. 4D*

```
F   1                                     MRLPG------------VPLAR  10
    1  MILKEEHPHQSIETAANAARQAQVRWRMAHLKALSRTRTPAHGNCCGRVVSKNHFFKHSR  60

F  11  PALLLLLPLLAPLLGTGAPAELRVRVRLPDGQVTEESLQADSDADSISLELRKPDGILVS  70
   61  AFLWFLLCNLVMNADAFAHSQLLINVQNQGGEVTQESITSNIGEDLITLEFQKTDGILIT  120

F  71  FTADIKKDVKVFRALILGELKKGQSQFQALCFVTQLDHNEIIPSEAMAKLRQKNPRAVRQ  130
  121  QVIDIRNEVQILKALVLGEEKRGQSQYQWMCFATKFNKGDFISSAAMAKLRQKNPHTIRT  180

F 131  AEEVRGLEHLHMDVAVNFSQGALLSPHLHNVCAEAVDAIVTRQEDVRFWLED-GVDSSVF  189
  181  REEDKGRETFTMSSWVQLNRSLPITRHLQGLCAEAMDATVVRDVDLKAWAELRGSSISSL  240

F 190  KALPKASEQAELPRCRQVGDRGKPCVCHYGLSLAWVPCMLKVCHSR----D-------   236
  241  KAATEKFPDTLSTRCNEVSSLWAPCLCNLETCIGWVPGLKVCKGKGVAGADSSGAQQQA  300

F 237  RPTPVKCGIRSCQKSYSFDFVVPQRQLCLWDEDPYPG   273
  301  QPTNVRCGIKTCRKTQFTYVVRQKQCCLWDE          332
```

*Fig. 7*

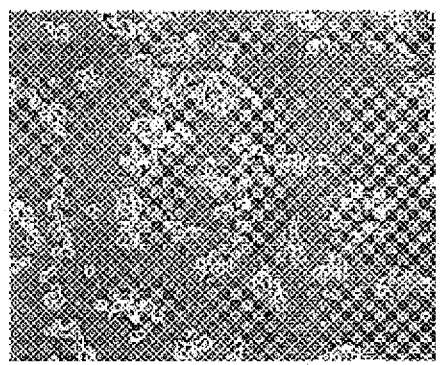
AS
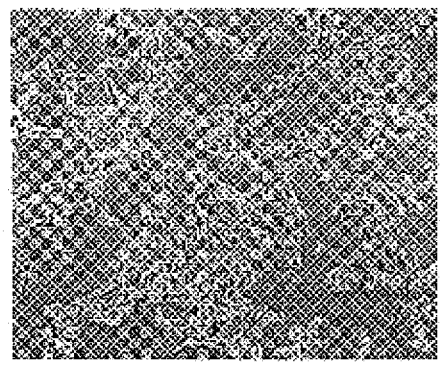
RC
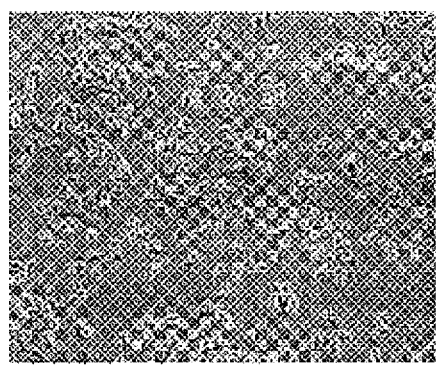
AS+M
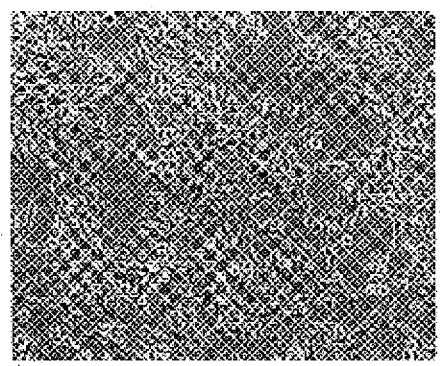
Normal
*Fig. 10A*

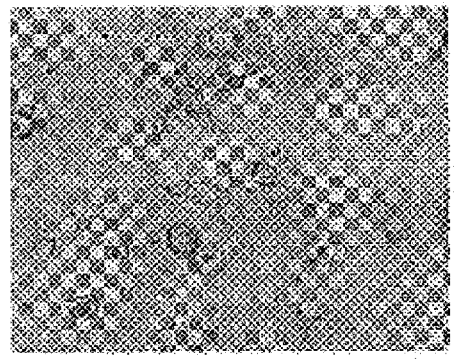
AS
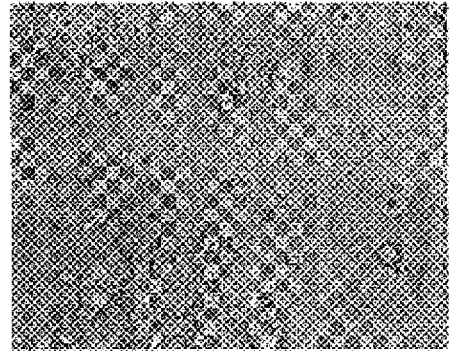
RC
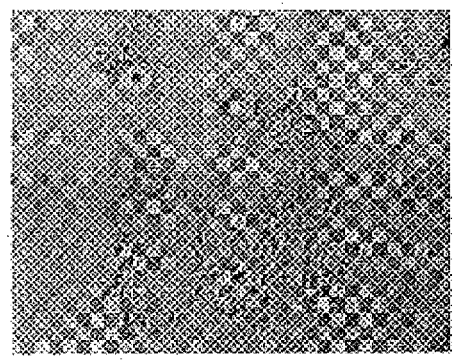
AS+M
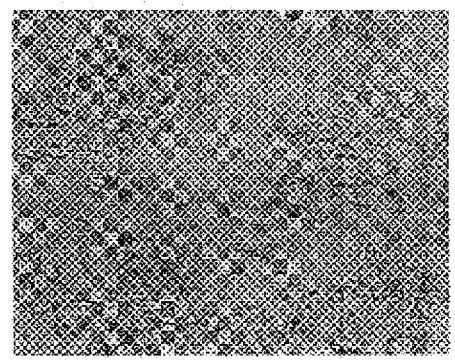
Normal
*Fig. 10B*

```
   1 ccgcgaggtgcgcggtctctttaaggcgggtcctggtggtttctgtttcctgaaggaagtgacggggggtgggattgaatgaaaagtg
  89 caaaacacaggctcgcagcgctggagcccggggccgcggagccgggccggggcagcgccgtctccgcctcggggccgccgggggcgccct
 179 GCTGAGCGCTACCCACGTGCGTCCGCGCCACCTCGCGGGCGACCCCGCGGCCAAGGCCCCCGGCGGAGCGGCTCCCGGGCGCCCCGAACT
 269 AGCCCCCAACTTTGGGCGAAGTTTGCCTGCGCCTCTCCCCGCCCCACGCGGCGCGCCGGGGCCGCGGACGGCAGCGGCCCCCGGGGATG
   1                                                                                        m
 359 CGCCTTCCCGGGGTACCCCTGGCGCGCCCTGCGCTGCTGCTGCTGCTGCCGCTGCTCGCGCCGCTGCTGGGAACGGGTGCGCCGGCCGAG
   2  R  L  P  G  V  P  L  A  R  P  A  L  L  L  L  L  P  L  L  A  P  L  L  G  T  G  A  P  A  E
 449 CTGCGGGTCCGCGTGCGGCTGCCGGACGGCCAGGTGACCGAGGAGAGCCTGCAGGCGGACAGCGACGCGGACAGCATCAGCCTCGAGCTG
  32  L  R  V  R  V  R  L  P  D  G  Q  V  T  E  E  S  L  Q  A  D  S  D  A  D  S  I  S  L  E  L
 539 CGCAAGCCCGACGGCACCCTCGTCTCCTTCACCGCCGACTTCAAGAAGGATGTGAAGGTCTTCCGGGCCCTGATCCTGGGGGAGCTGGAG
  62  R  K  P  D  G  T  L  V  S  F  T  A  D  F  K  K  D  V  K  V  F  R  A  L  I  L  G  E  L  E
 629 AAGGGGCAGAGTCAGTTCCAGGCCCTCTGCTTTGTCACCCAGCTGCAGCACAATGAGATCATCCCCAGTGAGGCCATGGCCAAGCTCCGG
  92  K  G  Q  S  Q  F  Q  A  L  C  F  V  T  Q  L  Q  H  N  E  I  I  P  S  E  A  M  A  K  L  R
 719 CAGAAAAATCCCCGGGCAGTGCGGCAGGCGGAGGAGGTTCGGGGTCTGGAGCATCTGCACATGGATGTCGCTGTCAACTTCAGCCAGGGG
 122  Q  K  N  P  R  A  V  R  Q  A  E  E  V  R  G  L  E  H  L  H  M  D  V  A  V  N  F  S  Q  G
 809 GCCCTGCTGAGCCCCCATCTCCACAACGTGTGTGCCGAGGCCGTGGATGCCATCTACACCCGCCAGGAGGATGTCCGGTTCTGGCTGGAG
 152  A  L  L  S  P  H  L  H  N  V  C  A  E  A  V  D  A  I  Y  T  R  Q  E  D  V  R  F  W  L  E
 899 CAAGGTGTGGACAGTTCTGTGTTCGAGGCTCTGCCCAAGGCCTCAGAGCAGGCGGAGCTGCCTCGCTGCAGGCAGGTGGGGGACCGCGGG
 182  Q  G  V  D  S  S  V  F  E  A  L  P  K  A  S  E  Q  A  E  L  P  R  C  R  Q  V  G  D  R  G
 989 AAGCCCTGCGTCTGCCACTATGGCCTGAGCCTGGCCTGGTACCCCTGCATGCTCAAGTACTGCCACAGCCGCGACCGGCCCACGCCCTAC
 212  K  P  C  V  C  H  Y  G  L  S  L  A  W  Y  P  C  M  L  K  Y  C  H  S  R  D  R  P  T  P  Y
1079 AAGTGTGGCATCCGCAGCTGCCAGAAGAGCTACAGCTTCGACTTCTACGTGCCCCAGAGGCAGCTGTGTCTCTGGGATGAGGATCCCTAC
 242  K  C  G  I  R  S  C  Q  K  S  Y  S  F  D  F  Y  V  P  Q  R  Q  L  C  L  W  D  E  D  P  Y
1169 ccaggctagggtgggagcaacctgggcgggtggctgctctgggcccactgctcttcaccagccactagagggggtggcaaccccccacctg
 272  p  g  *
1259 aggccttatttccctccctcccactccctggccctagagcctgggcccCtctggccccatctcacatgactgtgaaggggtgtggca
1349 tggcagggggtctcatgaaggcaccccattcccacccgtgccttccttgcgggcagagagggagagaagggctccccagatctacacc
1439 cctccctcctgcatctcccctggagtgttcacttgcaagctgccaaaacatgatggcctctggttgttctgttgaactccttgaacgttt
1529 agaccctaaaaggagtctatacctggacacccacctcccccagacacaactcccttccccatgcacacatctggaaggagctggccccctca
1619 gtccttcctactccccaacaaggggctcactatccccaaagaaggagctgttggggacccacgacgcagcccctgtactggattacagc
1709 atattctcatctctggccccgaggctgcctgtggggcgagtggagacctcccatcactgagacagatcacagaccacgagtgcctttccc
1799 ggacctggacgttgcctccaaaacaggcaccagctctttccctctctagacagaaatattttttgtaaggttctggggcagggaggagca
1889 tgaagtacgaggaaaacttgaattccagatttttaatgcaaagtatttatcatttctaccagaaataaacgttttaagttttacttgac
1979 taatgagacccagagtttggagaaaacttttggccaatgctgccacctgatgtcagaaagtgtccccacaccctagcagtggcctatctt
2069 ggaacaagaacttcgaaagcacctactgtgtgctcagccatttgaggaaggaaggaggagaaggaagatgttactagggaaggatgagat
2159 aaaacttctgcacccaagacaatgagacagacataactgcaaccgtagtaagccagtcagaaatagccagcgcgaaggcaagagatgggg
2249 tggagattggaaccccgcttcagatctgggctcggctacttacctgctgtgcagccatgggtcaagttgcttgacctctctgtgcctcca
2339 ctcccttagctataaaatgagcttactt-polyA
```

*Fig. 11*

GENES DIFFERENTIALLY EXPRESSED IN BREAST CANCER

CROSS-REFERENCE TO RELATED APPLICATIONS

This application claims priority from U.S. Patent Application No. 60/175,462 filed Jan. 10, 2000, which is incorporated by reference herein in its entirety.

TECHNICAL FIELD

This invention relates to methods for predicting the behavior of tumors. More particularly, the invention relates to methods in which a tumor sample is examined for expression of a specified gene sequence thereby to indicate propensity for metastatic spread.

BACKGROUND OF THE INVENTION

Breast cancer is one of the most common malignant diseases with about 1,000,000 new cases per year worldwide. Despite use of a number of histochemical, genetic, and immunological markers, clinicians still have a difficult time predicting which tumors will metastasize to other organs. Some patients are in need of adjuvant therapy to prevent recurrence and metastasis and others are not. However, distinguishing between these subpopulations of patients is not straightforward, and course of treatment is not easily charted. There is a need in the art for new markers for distinguishing between tumors which will or have metastasized and those which are less likely to metastasize

SUMMARY OF THE INVENTION

It is an object of the present invention to provide markers for distinguishing between tumors which will or have metastasized and those which are less likely to metastasize. These and other objects of the invention are provided by one or more of the embodiments described below.

One embodiment of the invention provides an isolated and purified human protein having an amino acid sequence which is at least 85% identical to an amino acid sequence encoded by the nucleotide sequence of SEQ ID NO:1 or the complement thereof.

Another embodiment of the invention provides a fusion protein which comprises a first protein segment and a second protein segment fused to each other by means of a peptide bond. The first protein segment consists of at least six contiguous amino acids selected from an amino acid sequence encoded by a nucleotide sequence SEQ ID NO:1 or the complement thereof, and the second protein segment comprises an amino acids sequence not found adjacent to the first protein segment in the native protein encoded by SEQ ID NO:1.

Yet another embodiment of the invention provides an isolated and purified polypeptide consisting of at least six contiguous amino acids of a human protein having an amino acid sequence encoded by a nucleotide sequence of SEQ ID NO:1 or the complement thereof.

Still another embodiment of the invention provides a preparation of antibodies which specifically bind to a human protein which comprises an amino acid sequence encoded by a nucleotide sequence of SEQ ID NO:1 or the complement thereof.

Even another embodiment of the invention provides an isolated and purified subgenomic polynucleotide comprising at least 11 contiguous nucleotides of a nucleotide sequence which is at least 95% identical to a nucleotide sequence of SEQ ID NO:1 or the complement thereof.

Another embodiment of the invention provides an isolated and purified polynucleotide which comprises a coding sequence comprising a nucleotide sequence of SEQ ID NO:1 or the complement thereof.

Yet another embodiment of the invention provides a method for determining metastasis in a tissue sample. An expression product of a gene which comprises a coding sequence of SEQ ID NO:1 is measured in a tissue sample. A tissue sample which expresses the product at a higher level than in a control sample is categorized as having greater metastatic potential.

Yet a further embodiment of the invention provides a method for detecting a human gene encoding SEQ ID NO:2, the method comprising obtaining in computer-readable format SEQ ID NO:1, comparing the sequence with polynucleotide sequences of a human genome, and identifying one or more human genome sequences having at least 95% sequence identity to SEQ ID NO:1 as determined by the Smith-Waterman algorithm using an affine gap search with a gap open penalty of 12 and a gap extension penalty of 1 as parameters.

The invention thus provides the art with a number of polynucleotides and polypeptides, which can be used as markers of metastasis. These are useful for more rationally prescribing the course of therapy for breast cancer patients.

BRIEF DESCRIPTION OF THE DRAWINGS

FIG. 1 illustrates the polynucleotide sequence of human Out at First (SEQ ID NO:1).

FIG. 2 illustrates the amino acid sequence encoded by SEQ ID NO:1 (SEQ ID NO:2).

FIG. 3 illustrates the putative signal peptide (SEQ ID NO:3).

FIG. 4 illustrates the translation of SEQ ID NO:1 (SEQ ID NO:1, polynucleotide; SEQ ID NO:2, amino acid sequence).

FIG. 7 is an alignment of the human OAF amino acid sequence (SEQ ID NO: 6) with the Drosophila OAF amino acid sequence (SEQ ID NO: 7).

FIG. 8.

FIG. 10. FIG. 10A illustrates the morphological changes seen in MDA-MB-435 cells following treatment with antisense oligo (SEQ ID NO:4). AS=antisense; RC=reverse control (SEQ ID NO:5); M=conditioned medium. FIG. 10B illustrates cell invasion following treatment of MDA-MB-435 cells with AS, RC and RC+M.

FIG. 11 illustrates the predicted signal sequence of human OAF (SEQ ID NO: 9) (double underline), DNA sequence (SEQ ID NO: 8).

FIG. 12.

DETAILED DESCRIPTION OF THE INVENTION

Figure 5:
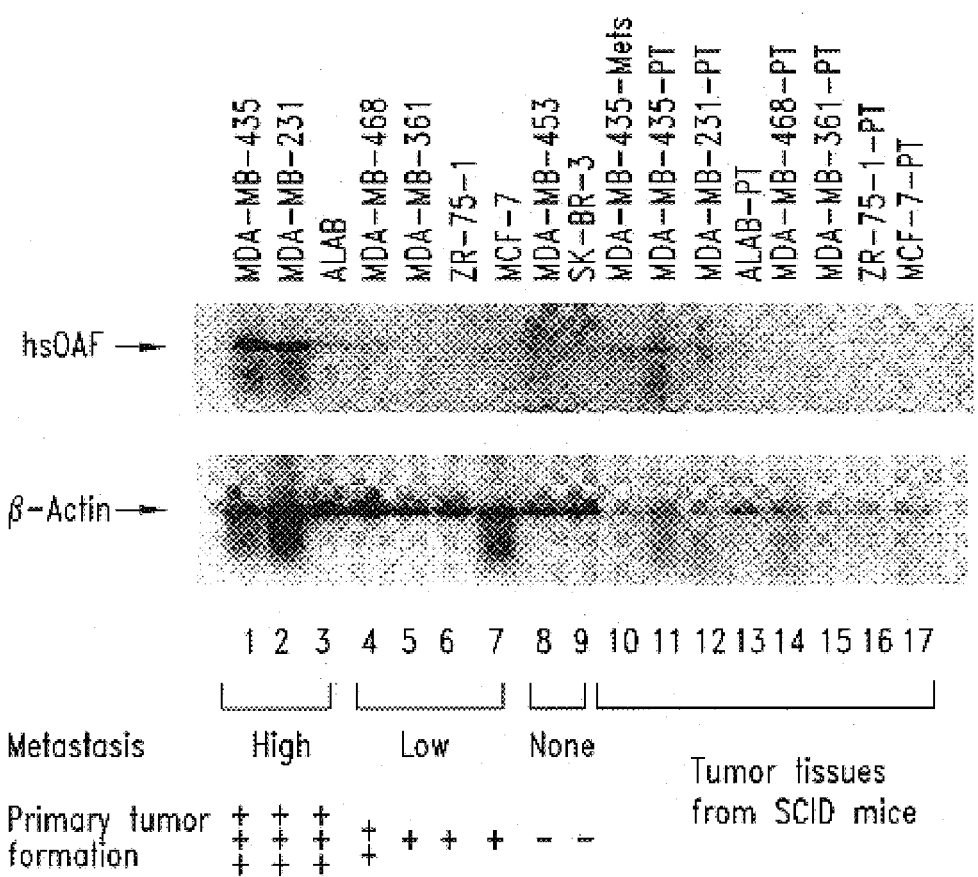
FIG. 5 illustrates the expression of hsOAF relative to β-Actin in tumor cell lines and tumor tissues from SCID mice developed from the cell lines. "PT" refers to primary tumor.

The most lethal cause in patients with breast cancer is the metastasis of breast carcinomas and their proliferation at distant loci (lung and bone, mainly). Metastasis is a multistep process by which tumor cells emigrate from the primary tumor, disseminate through blood and lymph vessels, and then are deposited in specific target organs where they re-colonize. Schirrmacher, V., *Adv. Cancer Res.* 43:1-73, 1985 and Liotta, L. A. et al., *Cell* 64(2):327-36 (1991). During this process the invasiveness of tumor cells is crucial since they must encounter and pass through numerous basement membranes. Liotta, L. A., *Am. J. Pathol.* 117(3):339-48 (1984) and Fidler, I. J., *Cancer Res.* 38(9):2651-60 (1978). Therefore the elucidation of the molecular causes of tumor cell invasion and metastasis is essential for the development of efficient treatment procedures for breast cancer patients. Genes differentially expressed in breast tumor metastasis are potential targets that play critical roles during metastasis. Identification of such genes and their biological function will significantly contribute to the development of therapy and diagnosis for breast cancer.

Some important genes involved in breast tumor metastasis have been discovered. Loss of estrogen receptor and presence of vimentin have been associated with human breast tumor invasiveness and poor prognosis, and also correlate with the invasiveness and metastatic potential of human breast cancer cell lines. Aamdal S., et al., *Cancer* 53(11):2525-9 (1984); Clark, G. M., et al., *Semin Oncol.*, 2 Suppl 1:20-5 (1988); Raymond, W. A. et al., *J. Pathol.* 157(4):299-306 (1989); Raymond, W. A., et al., *J. Pathol.* 158(2):107-14 (1989); and Thompson, E. W. et al., *J. Cell Physiol.* 150(3):534-44 (1992). E-cadherin underexpression has been implicated in mammary tumor invasiveness. Vleminckx, K., et al., *Cell* 66(1):107-19 (1991) and Oka, H., et al., *Cancer Res.* 53(7): 1696-701 (1993). Maspin, a protease inhibitor expressed in normal mammary epithelial cells' but not in most breast carcinoma cell lines, was able to suppress MDA-MB-435 cells ability to induce tumors and metastasize in mice and to invade basement membrane in vitro. Loss of maspin expression occurred most frequently in advanced cancers. Zou, Z., et al., *Science* 263(5146):526-9 (1994) and Seftor, R. E., et al., *Cancer Res.* 58(24):5681-5 (1998).

Overexpression of TIMP-4 (tissue inhibitor of metalloproteinases-4) or CLCA2 ($Ca^{2+}$-activated chloride channel-2) in MDA-MB-435 cells by transfection inhibited the tumorigenicity, invasiveness and metastasis ability of the cells. Wang, M., et al., *Oncogene* 14(23):2767-74 (1997) and Gruber, A. D., et al., *Cancer Res.* 59(21):5488-91 (1999). Overexpression of the growth factor receptors IGF-IR and $p185^{ErbB-2}$ has been found to be involved in breast cancer metastasis. Surmacz, E., et al., *Breast Cancer Res. Treat* 47(3):255-67 (1998); Dunn, S. E., et al., *Cancer Res.* 58(15):3353-61 (1998); Tan, M., et al., *Cancer Res.* 57(6):1199-205 (1997); Dhingra, K., et al., *Semin Oncol.* 23(4):436-45 (1996); and Revillion, F., et al., *Eur. J. Cancer* 34(6):791-808 (1998).

The aspartyl protease cathepsin D has been reported to be a marker of poor prognosis for breast cancer patients and there is a significant correlation between high cathepsin D concentration in the cytosol of primary breast cancer and development of metastasis, though no correlation was found between cathepsin D secretion and invasion ability of breast cancer cell lines. Rochefort, H., *Breast Cancer Res Treat* 16(1):3-13 (1990); Johnson, M. D., et al., *Cancer Res.* 53(4): 873-7 (1993); and Rochefort, H., et al., *Clin Chim Acta.* 29(2):157-70 (2000). Osteopontin, a secreted integrin-binding glycoprotein that is thought to be involved in bone resorption and bone formation, can induce migration and invasion of mammary carcinoma cells. Osteopontin levels (tumor cell or plasma levels) have been associated with enhanced malignancy of breast cancer. Denhardt, D. T., et al., *FASEB J.* 7(15):1475-82 (1993); Denhardt, D. T., et al., *J. Cell Biochem Suppl.*, 30-31:92-102 (1998); Tuck, A. B., et al., *J. Cell Biochem.* 78(3):465-75 (2000); Tuck, A. B., et al., *Oncogene* 18(29):4237-46 (1999); and Singhal, H., et al., *Clin Cancer Res.* 3(4):605-11 (1997).

The invention relates to the cloning of a novel gene overexpressed in highly metastatic human breast cancer cell lines. It encodes a secreted protein and its protein secretion has been confirmed to be much greater in highly metastatic human breast cancer cell lines than in low metastatic/nonmetastatic cell lines. Knockout of the secretion of this protein of the aggressive MDA-MB-435 cell line by antisense oligo technology resulted in significant morphological alteration along with reduced invasiveness and proliferation rate of the cells. The gene is named hsOAF based on its homology with the *Drosophila* gene OAF (out at first). Bergstrom, D. E., et al., *Genetics* 139(3):1331-46 (1995) and Merli, C., et al., *Genes Dev.* 10(10):1260-70 (1996)

It is a discovery of the present invention that a polynucleotide is differentially expressed between high metastatic breast cancer cells and non-metastatic or low metastatic cancer cells. This polynucleotide therefore relates to a metastatic marker gene. This information can be utilized to make diagnostic reagents specific for the expression products of the differentially expressed gene. It can also be used in diagnostic and prognostic methods which will help clinicians in planning appropriate treatment regimes for cancers, especially of the breast.

The polynucleotide is shown in FIG. 1 (SEQ ID NO:1), and the predicted open reading frame (ORF) encodes a polypeptide shown in FIG. 2 (SEQ ID NO:2). The first 30 amino acid residues (SEQ ID NO:3) comprise a putative signal peptide, with a predicted protease cleavage site indicated by "*": APLLG*TGAPA (SEQ ID NO: 10) (between amino acids at positions 25 and 26 of SEQ ID NO:3).

The polynucleotide sequence of the invention shares some homology with a Drosophila gene known as "Out at First" (oaf). Transcription of oaf results in three classes of alternatively polyadenylated RNAs, the expression of which is developmentally regulated. All oaf transcripts contain two adjacent ORFs separated by a single UGA stop codon. Suppression of the UGA codon during translation could lead to the production of different proteins from the same RNA molecule. During oogenesis, oaf RNA is expressed in nurse cells of all ages, and is maternally contributed to the egg.

During embryonic development, zygotic transcription of the oaf gene occurs in small clusters of cells in most or all segments at the time of germband extension and later in a segmentally repeated pattern in the developing central nervous system. The oaf gene is also expressed in the embryonic, larval and adult gonads of both sexes. (Bergstrom, D. E. et al., *Genetics* 139:1331-1346, 1995.)

The polynucleotide of the invention was differentially expressed in seven pairs of high metastatic versus non-metastatic or low metastatic breast cancer cell lines. The cell lines used are MDA-MB-361 (derived from human breast adenocarcinoma), MDA-MB-231 (human breast cancer cells metastatic to bone and/or lung); MDA-MB-468 (derived from human estrogen receptor-negative breast cancer cells); MCF-7 (non-metastatic human breast cancer cells); ZR-75-1 (derived from estrogen receptor-positive human breast carcinomas, Engle et al., *Cancer Res.* 38:3352-64 (1978)); and MDA-MB-435 (derived from estrogen receptor-negative human breast carcinoma cells, Rishi et al., *Cancer Res.* 56:5246-5252 (1996)).

The expression profile is as follows:

TABLE 1

| Cell Line Pair | Ratio of Expression |
| --- | --- |
| MDA-MB-361/MDA-MB-231 | 0.11 |
| MDA-MB-468/MDA-MB-231 | 0.44 |
| MCF-7/MDA-MB-231 | 0.17 |
| ZR-75-1/MDA-MB-231 | 0.12 |
| MDA-MB-361/MDA-MB-435 | 0.06 |
| MDA-MB-468/MDA-MB-435 | 0.36 |
| MCF-7/MDA-MB-435 | 0.03 |

The upregulation of the mRNA expression was confirmed by Northern blot analysis using total RNA from the cell lines (FIG. 5).

The cell lines in which expression of the polynucleotide of the invention was compared represent human breast cancers of varying metastatic potential. Cell line ZR-75-1 cultures were derived from malignant ascitic effusion of a breast cancer patient. The cell lines grown in vitro closely resembled the morphology seen in biopsies or cell preparations from the donors of the original cells. ZR-75-1 cells are specifically stimulated by estrogen, and have been used as a model system for studying estrogen responsiveness. Engel, L. W. et al., *Cancer Res.* 38:3352-3364, 1978.

Cell line MDA-MB-435 is an estrogen receptor-negative cell line that has been studied as a model for human breast cancer, for example, for studying the mechanism of action of growth inhibition in the presence of retinoic acid. Rishi, A. K. et al., *Cancer Res.* 56:5246-5252, 1996. Growth inhibition by retinoids has also been studied in MCF-7 cells and MDA MB 468 cells. Tin-U, C. K. et al., *Am. Soc. Clin. Onc. Proceedings*, Vol. 17,2125, 1998.

Cell line MDA-MB-361 was derived from a human breast adenocarcinoma, specifically from a malignant site. ATCC Number HTB-27. Differential expression of human Wnt genes has been studied in this cell line. Huguet, E. L. et al., *Cancer Res.* 54:2615-2621, 1994.

Once metastasis occurs, mammary primary tumor cells invade basement membranes and spread to other organs of the body and the survival chance of patients with breast cancer becomes quite slim. It is critical to identify genes participating in breast cancer invasion and metastasis on behalf of clinical diagnosis and therapy. Such genes are potential markers for diagnosis or candidate targets for therapeutic drug development. For instance, presence of vimentin in human breast tumor has been associated with lack of estrogen receptor and tumor invasiveness as a marker of poor prognosis. Raymond, W. A. et al., *J. Pathol.* 157(4):299-306 (1989); Raymond, W. A., et al., *J. Pathol.* 158(2):107-14 (1989); and Thompson, E. W. et al., *J. Cell Physiol.*150(3):534-44 (1992). Increased activities of matrix metalloproteinases are related with the metastatic phenotype of carcinomas, especially breast cancer. Basset, P., et al., *Nature* 348(6303):699-704 (1990) and Basset, P., et al., *Cancer* 74(3 Suppl):1045-9 (1994). Osteopontin, a secreted integrin-binding glycoprotein, is able to induce increased invasiveness of human mammary epithelial cells and has been associated with enhanced malignancy in breast cancer. Tuck, A. B., et al., *J. Cell Biochem.* 78(3):465-75 (2000); Tuck, A. B., et al., *Oncogene* 18(29):4237-46 (1999); and Singhal, H., et al., *Clin Cancer Res.* 3(4):605-11 (1997).

The invention relates to identification of a novel secreted protein (hsOAF) involved in breast cancer metastasis. The human breast cancer cell lines used in elucidating the role of the protein are divided into three groups according to their metastatic abilities: highly metastatic, low metastatic, and nonmetastatic. Taking advantage of different metastatic potentials among these cell line groups and utilizing the advanced microarray technology, genes were identified which are differentially expressed between highly metastatic human breast cancer cell lines and low metastatic/nonmetastatic ones. These genes are good candidates for expression validation and function studies that could lead to better understanding of the molecular mechanism of breast cancer metastasis. hsOAF gene is the focus of this invention as it encodes a novel secreted protein. hsOAF mRNA expression is quite common in various human normal tissues. However, hsOAF protein secretion is much stronger by highly metastatic human breast cancer cell lines than by low metastatic/nonmetastatic ones, and MDA-MB-435 has the greatest hsOAF secretion. hsOAF gene was named based on its homology with the *Drosophila* OAF (out at first) gene. However, the *Drosophila* OAF protein may not be a secreted protein since it does not possess a typical signal peptide sequence at N-terminus (FIG. 7).

To address the importance of secreted hsOAF protein in breast cancer metastasis, antisense oligo technology was used to specifically knock out hsOAF expression. Antisense oligo technology is an efficient, fast way to dramatically reduce gene expression for gene functional studies. Stein, C. A., et al., *Science* 261(5124):1004-12 (1993); Defacque, H. et al., *J. Cell Physiol.* 178(1):109-19 (1999). Knockout of hsOAF protein secretion of highly metastatic MDA-MB-435 cells resulted in cell shape change, reduced cell invasiveness and slower cell proliferation. Treatment of cells with the conditioned medium (culture medium of normal MDA-MB-435 cells) was able to recover all those phenotypic alterations caused by the knockout of hsOAF protein secretion to some degree. Although the inventors are not bound by a specific mechanism, the secreted hsOAF protein is believed to be essential for the invasiveness and proliferation of MDA-MB-435 cells. However, knockout of hsOAF protein secretion of another highly metastatic cell line, MDA-MB-231, by antisense oligo technology did not cause any significant cellular changes. MDA-MB-435 and MDA-MB-231 are quite different metastatic cell lines and MDA-MB-435 shows much stronger hsOAF protein secretion than does MDA-MB-213.

hsOAF gene is located at chromosome 11q23 region where loss of heterozygosity occurs frequently in human breast tumors. Negrini, M., et al., *Cancer Res* 55(14):3003-7 (1995) and Tomlinson, I. P., et al., *J. Clin. Pathol.* 48(5):424-8 (1995). Loss of heterozygosity at 11q23 in primary human breast tumors has been reported to be associated with poor survival after metastasis. Winqvist, R., et al., *Cancer Res.* 55(12):2660-4 (1995). 11q23 also contains loci such as ATM (Ataxia-telangiectasia, mutated), and MLL (which is frequently disrupted by chromosomal rearrangement in acute leukemia). Rasio, D., et al., *Cancer Res.* 55(24):6053-7 (1995) and Rubnitz, J. E., et al., *Leukemia* 10(1):74-82 (1996). The relationship between mutation at chromosome 11q23 and hsOAF gene expression in breast cancer metastasis remains unclear.

Secreted hsOAF protein may be a suitable target for drug development against breast cancer and a good diagnostic marker for the malignancy of breast tumor. SEQ ID NO:1 and polynucleotides comprising this sequence are therefore useful as metastatic markers. Reference to metastatic marker nucleotide or amino acid sequences includes variants which have similar expression patterns in high metastatic relative to non-metastatic or low metastatic cells. Metastatic marker polypeptides can differ in length from full-length metastatic marker proteins and contain at least 6, 8, 10, 12, 15, 18, 20, 25, 30, 35, 40, 45, 50, 55, 60, 65, 70, 75, 80, 85, 90, 95, 100, 120, 140, 160, 180, 200, 220, 240, 260, 265, 270 or 271 or more contiguous amino acids of a metastatic marker protein. Exemplary polynucleotides include those encoding amino acids from about 1 to about 273; from 1 to 273; from about 2 to about 273; from 2 to 273; from about 26 to about 273; and from 26 to 273 of SEQ ID NO:2.

Variants of marker proteins and polypeptides can also occur. Metastatic marker protein or polypeptide variants can be naturally or non-naturally occurring. Naturally occurring metastatic marker protein or polypeptide variants are found in humans or other species and comprise amino acid sequences which are substantially identical to a protein encoded by a gene corresponding to the nucleotide sequence shown in SEQ ID NO:1 or its complement. Non-naturally occurring metastatic marker protein or polypeptide variants which retain substantially the same differential expression patterns in high metastatic relative to low-metastatic or non-metastatic breast cancer cells as naturally occurring metastatic marker protein or polypeptide variants are also included here. Preferably, naturally or non-naturally occurring metastatic marker protein or polypeptide variants have amino acid sequences which are at least 85%, 90%, 91%, 92%, 93%, 94%, or 95% identical to amino acid sequences encoded by the nucleotide sequence shown in SEQ ID NO:1. More preferably, the molecules are at least 96%, 97%, 98% or 99% identical. Percent sequence identity between a wild-type protein or polypeptide and a variant is determined by aligning the wild-type protein or polypeptide with the variant to obtain the greatest number of amino acid matches, as is known in the art, counting the number of amino acid matches between the wild-type and the variant, and dividing the total number of matches by the total number of amino acid residues of the wild-type sequence.

Preferably, amino acid changes in metastatic marker protein or polypeptide variants are conservative amino acid changes, i.e., substitutions of similarly charged or uncharged amino acids. A conservative amino acid change involves substitution of one of a family of amino acids which are related in their side chains. Naturally occurring amino acids are generally divided into four families: acidic (aspartate, glutamate), basic (lysine, arginine, histidine), non-polar (alanine, valine, leucine, isoleucine, proline, phenylalanine, methionine, tryptophan), and uncharged polar (glycine, asparagine, glutamine, cystine, serine, threonine, tyrosine) amino acids. Phenylalanine, tryptophan, and tyrosine are sometimes classified jointly as aromatic amino acids.

It is reasonable to expect that an isolated replacement of a leucine with an isoleucine or valine, an aspartate with a glutamate, a threonine with a serine, or a similar replacement of an amino acid with a structurally related amino acid will not have a major effect on the biological properties of the resulting metastatic marker protein or polypeptide variant. Properties and functions of metastatic marker protein or polypeptide variants are of the same type as a metastatic marker protein or polypeptide comprising amino acid sequences encoded by the nucleotide sequence shown in SEQ ID NO:1, although the properties and functions of variants can differ in degree. Whether an amino acid change results in a metastatic marker protein or polypeptide variant with the appropriate differential expression pattern can readily be determined. For example, nucleotide probes can be selected from the marker gene sequences disclosed herein and used to detect marker gene mRNA in Northern blots or in tissue sections, as is known in the art. Alternatively, antibodies which specifically bind to protein products of metastatic marker genes can be used to detect expression of metastatic marker proteins or variants thereof.

Metastatic marker variants include glycosylated forms, aggregative conjugates with other molecules, and covalent conjugates with unrelated chemical moieties. Metastatic marker variants also include allelic variants, species variants, and muteins. Truncations or deletions of regions which do not affect the differential expression of metastatic marker genes are also metastatic marker variants. Covalent variants can be prepared by linking functionalities to groups which are found in the amino acid chain or at the N- or C-terminal residue, as is known in the art.

It will be recognized in the art that some amino acid sequence of the polypeptide of the invention can be varied without significant effect on the structure or function of the protein. If such differences in sequence are contemplated, it should be remembered that there are critical areas on the protein which determine activity. In general, it is possible to replace residues that form the tertiary structure, provided that residues performing a similar function are used. In other instances, the type of residue may be completely unimportant if the alteration occurs at a non-critical region of the protein. The replacement of amino acids can also change the selectivity of binding to cell surface receptors. Ostade et al., *Nature* 361:266-268 (1993) describes certain mutations resulting in selective binding of TNF-alpha to only one of the two known types of TNF receptors. Thus, the polypeptides of the present invention may include one or more amino acid substitutions, deletions or additions, either from natural mutations or human manipulation.

The invention further includes variations of the disclosed polypeptide which show comparable expression patterns or which include antigenic regions. Such mutants include deletions, insertions, inversions, repeats, and type substitutions. Guidance concerning which amino acid changes are likely to be phenotypically silent can be found in Bowie, J. U., et al., "Deciphering the Message in Protein Sequences: Tolerance to Amino Acid Substitutions," *Science* 247:1306-1310 (1990).

Of particular interest are substitutions of charged amino acids with another charged amino acid and with neutral or negatively charged amino acids. The latter results in proteins with reduced positive charge to improve the characteristics of the disclosed protein. The prevention of aggregation is highly desirable. Aggregation of proteins not only results in a loss of activity but can also be problematic when preparing pharmaceutical formulations, because they can be immunogenic. (Pinckard et al., *Clin. Exp. Immunol.* 2:331-340 (1967); Robbins et al., *Diabetes* 36:838-845 (1987); Cleland et al., *Crit. Rev. Therapeutic Drug Carrier Systems* 10:307-377 (1993)).

Amino acids in the polypeptides of the present invention that are essential for function can be identified by methods known in the art, such as site-directed mutagenesis or alanine-scanning mutagenesis (Cunningham and Wells, *Science* 244:1081-1085 (1989)). The latter procedure introduces single alanine mutations at every residue in the molecule. The resulting mutant molecules are then tested for biological activity such as receptor binding, or in vitro proliferative activity. Sites that are critical for ligand-receptor binding can also be determined by structural analysis such as crystallization, nuclear magnetic resonance or photoaffinity labeling (Smith et al., *J. Mol. Biol.* 224:899-904 (1992) and de Vos et al. *Science* 255:306-312 (1992)).

As indicated, changes are preferably of a minor nature, such as conservative amino acid substitutions that do not significantly affect the folding or activity of the protein. Of course, the number of amino acid substitutions a skilled artisan would make depends on many factors, including those described above. Generally speaking, the number of substitutions for any given polypeptide will not be more than 50, 40, 30, 25, 20, 15, 10, 5 or 3.

Full-length metastatic marker proteins can be extracted, using standard biochemical methods, from metastatic marker protein-producing human cells, such as metastatic breast cancer cells. An isolated and purified metastatic marker protein or polypeptide is separated from other compounds which normally associate with a metastatic marker protein or polypeptide in a cell, such as certain proteins, carbohydrates, lipids, or subcellular organelles. A preparation of isolated and purified metastatic marker proteins or polypeptides is at least 80% pure; preferably, the preparations are 90%, 95%, or 99% pure.

A human gene encoding SEQ ID NO:2 can be identified and isolated using methods know in the art. According to one method, SEQ ID NO:1 is prepared in a computer-readable format. The sequence is compared with polynucleotide sequences of a human genome, and one or more human genome sequences having at least 95% sequence identity to SEQ ID NO:1 are identified, for example by using the Smith-Waterman algorithm using an affine gap search with a gap open penalty of 12 and a gap extension penalty of 1 as parameters. Probes based on the regions of homology between SEQ ID NO:1 and the human genome sequences are prepared and used to isolate polynucleotides from human genomic DNA, using methods known in the art. As of the filing date a human polynucleotide corresponding to the full polynucleotide of SEQ ID NO:1 was not identified in the public databases. Thus, the invention includes human genomic DNA comprising the coding region of SEQ ID NO:1 and any untranslated regions which do not share homology with SEQ ID NO:1 but which are contiguous with homologous regions. Such genomic DNA includes but is not limited to introns, promoters, and other regulatory regions functionally associated with a human gene having a region encoding SEQ ID NO:2.

Metastatic marker proteins and polypeptides can also be produced by recombinant DNA methods or by synthetic chemical methods. For production of recombinant metastatic marker proteins or polypeptides, coding sequences selected from the nucleotide sequences shown in SEQ ID NO:1, or variants of those sequences which encode metastatic marker proteins, can be expressed in known prokaryotic or eukaryotic expression systems (see below). Bacterial, yeast, insect, or mammalian expression systems can be used, as is known in the art.

Alternatively, synthetic chemical methods, such as solid phase peptide synthesis, can be used to synthesize a metastatic marker protein or polypeptide. General means for the production of peptides, analogs or derivatives are outlined in CHEMISTRY AND BIOCHEMISTRY OF AMINO ACIDS, PEPTIDES, AND PROTEINS—A SURVEY OF RECENT DEVELOPMENTS, Weinstein, B. ed., Marcell Dekker, Inc., publ., New York (1983). Moreover, substitution of D-amino acids for the normal L-stereoisomer can be carried out to increase the half-life of the molecule. Metastatic marker variants can be similarly produced.

Non-naturally occurring fusion proteins comprising at least 6, 8, 10, 12, 15, 18, 20, 25, 30, 35, 40, 50, 55, 60, 65, 70, 75, 80, 85, 90, 95, 100, 120, 140, 160, 180, 200, 220, 240, 250, 260, 265, 270 or 271 or more contiguous metastatic marker amino acids can also be constructed. Human metastatic marker fusion proteins are useful for generating antibodies against metastatic marker amino acid sequences and for use in various assay systems. For example, metastatic marker fusion proteins can be used to identify proteins which interact with metastatic marker proteins and influence their functions. Physical methods, such as protein affinity chromatography, or library-based assays for protein-protein interactions, such as the yeast two-hybrid or phage display systems, can also be used for this purpose. Such methods are well known in the art and can also be used as drug screens.

A metastatic marker fusion protein comprises two protein segments fused together by means of a peptide bond. The first protein segment comprises at least 6, 8, 10, 12, 15, 18, 20, 25, 30, 35, 40, 50, 55, 60, 65, 70, 75, 80, 85, 90, 95, 100, 120, 140, 160, 180, 200, 220, 240, 250, 260, 265, 270 or 271 or more contiguous amino acids of a metastatic marker protein. The amino acids can be selected from the amino acid sequences encoded by the nucleotide sequence shown in SEQ ID NO:1 or from variants of the sequence, such as those described above. The first protein segment can also comprise a full-length metastatic marker protein.

In one preferred embodiment, the first protein segment comprises the polypeptide shown in SEQ ID NO:2. In a variation of this embodiment, the first protein segment consists of amino acids 31-287 of SEQ ID NO:2. This fusion protein lacks the signal peptide of SEQ ID NO:2 and would be suitable for retention of the expressed fusion protein inside the cell.

The second protein segment can be a full-length protein or a protein fragment or polypeptide not found adjacent to the first protein segment in the native protein encoded by SEQ ID NO:1. The fusion protein can be labeled with a detectable marker, as is known in the art, such as a radioactive, fluorescent, chemiluminescent, or biotinylated marker. The second protein segment can be an enzyme which will generate a detectable product, such as β-galactosidase. The first protein segment can be N-terminal or C-terminal, as is convenient.

Techniques for making fusion proteins, either recombinantly or by covalently linking two protein segments, are also well known. Recombinant DNA methods can be used to prepare metastatic marker fusion proteins, for example, by making a DNA construct which comprises coding sequences of SEQ ID NO:1 in proper reading frame with nucleotides encoding the second protein segment and expressing the DNA construct in a host cell, as described below. The open reading frame of SEQ ID NO:1 is shown in FIG. 4.

Isolated and purified metastatic marker proteins, polypeptides, variants, or fusion proteins can be used as immunogens, to obtain preparations of antibodies which specifically bind to a metastatic marker protein. The antibodies can be used, inter alia, to detect wild-type metastatic marker proteins in human tissue and fractions thereof. The antibodies can also be used to detect the presence of mutations in metastatic marker genes which result in under- or over-expression of a metastatic marker protein or in expression of a metastatic marker protein with altered size or electrophoretic mobility.

Preparations of polyclonal or monoclonal antibodies can be made using standard methods. Single-chain antibodies can also be prepared. A preferred immunogen is a polypeptide comprising SEQ ID NO:2. Single-chain antibodies which specifically bind to metastatic marker proteins, polypeptides, variants, or fusion proteins can be isolated, for example, from single-chain immunoglobulin display libraries, as is known in the art. The library is "panned" against metastatic marker protein amino acid sequences of SEQ ID NO:2, and a number of single chain antibodies which bind with high-affinity to different epitopes of metastatic marker proteins can be isolated. Hayashi et al., 1995, Gene 160:129-30. Single-chain antibodies can also be constructed using a DNA amplification method, such as the polymerase chain reaction (PCR), using hybridoma cDNA as a template. Thirion et al., 1996, *Eur. J. Cancer Prev.* 5:507-11.

Metastatic marker-specific antibodies specifically bind to epitopes present in a full-length metastatic marker protein having an amino acid sequence encoded by a nucleotide sequence shown in SEQ ID NO:1, to metastatic marker polypeptides, or to metastatic marker variants, either alone or as part of a fusion protein. Preferably, metastatic marker epitopes are not present in other human proteins. Typically, at least 6, 8, 10, or 12 contiguous amino acids are required to form an epitope. However, epitopes which involve non-contiguous amino acids may require more, e.g., at least 15, 25, or 50 amino acids.

Antibodies which specifically bind to metastatic marker proteins, polypeptides, fusion proteins, or variants provide a detection signal at least 5-, 10-, or 20-fold higher than a detection signal provided with other proteins when used in Western blots or other immunochemical assays. Preferably, antibodies which specifically bind to metastatic marker epitopes do not detect other proteins in immunochemical assays and can immunoprecipitate a metastatic marker protein, polypeptide, fusion protein, or variant from solution.

Subgenomic polynucleotides contain less than a whole chromosome. Preferably, the polynucleotides are intron-free. In a preferred embodiment, the polynucleotide molecules comprise a contiguous sequence of 10, 15, 20, 25, 30, 40, 50, 75, 100, 150, 200, 300, 400, 500, 600, 700, 800, 900, 1000, 1100, 1200, 1300, 1400, 1500, 1600, 1700, 1800, 1900, 2000, 2100, 2200, 2300 or 2350 nucleotides from SEQ ID NO:1 or the complements thereof. The complement of a nucleotide sequence shown in SEQ ID NO:1 is a contiguous nucleotide sequence which forms Watson-Crick base pairs with a contiguous nucleotide sequence shown in SEQ ID NO:1.

Degenerate nucleotide sequences encoding amino acid sequences of metastatic marker protein or variants, as well as homologous nucleotide sequences which comprise a polynucleotide at least 85%, 90%, 91%, 92%, 93%, 94%, 95%, 96%, 97%, 98%, or 99% identical to the coding region of the nucleotide sequence shown in SEQ ID NO:1, are also metastatic marker subgenomic polynucleotides. Typically, homologous metastatic marker subgenomic polynucleotide sequences can be confirmed by hybridization under stringent conditions, as is known in the art. Percent sequence identity between wild-type and homologous variant sequences is determined by aligning the wild-type polynucleotide with the variant to obtain the greatest number of nucleotide matches, as is known in the art, counting the number of nucleotide matches between the wild-type and the variant, and dividing the total number of matches by the total number of nucleotides of the wild-type sequence. A preferred algorithm for calculating percent identity is the Smith-Waterman homology search algorithm as implemented in MPSRCH program (Oxford Molecular) using an affine gap search with the following search parameters: gap open penalty of 12, and gap extension penalty of 1.

A metastatic marker subgenomic polynucleotide comprising metastatic marker protein coding sequences can be used in an expression construct. Preferably, the metastatic marker subgenomic polynucleotide is inserted into an expression plasmid (for example, the Ecdyson system, pIND, In vitro Gene). Metastatic marker subgenomic polynucleotides can be propagated in vectors and cell lines using techniques well known in the art. Metastatic marker subgenomic polynucleotides can be on linear or circular molecules. They can be on autonomously replicating molecules or on molecules without replication sequences. They can be regulated by their own or by other regulatory sequences, as are known in the art.

A host cell comprising a metastatic marker expression construct can then be used to express all or a portion of a metastatic marker protein. Host cells comprising metastatic marker expression constructs can be prokaryotic or eukaryotic. A variety of host cells are available for use in bacterial, yeast, insect, and human expression systems and can be used to express or to propagate metastatic marker expression constructs (see below). Expression constructs can be introduced into host cells using any technique known in the art. These techniques include transferrin-polycation-mediated DNA transfer, transfection with naked or encapsulated nucleic acids, liposome-mediated cellular fusion, intracellular transportation of DNA-coated latex beads, protoplast fusion, viral infection, electroporation, and calcium phosphate-mediated transfection.

A metastatic marker expression construct comprises a promoter which is functional in a chosen host cell. The skilled artisan can readily select an appropriate promoter from the large number of cell type-specific promoters known and used in the art. The expression construct can also contain a transcription terminator which is functional in the host cell. The expression construct comprises a polynucleotide segment which encodes all or a portion of the metastatic marker protein, variant, fusion protein, antibody, or ribozyme. The polynucleotide segment is located downstream from the promoter. Transcription of the polynucleotide segment initiates at the promoter. The expression construct can be linear or circular and can contain sequences, if desired, for autonomous replication.

Bacterial systems for expressing metastatic marker expression constructs include those described in Chang et al., *Nature* (1978) 275:615, Goeddel et al., *Nature* (1979) 281: 544, Goeddel et al., *Nucleic Acids Res.* (1980) 8:4057, EP 36,776, U.S. Pat. No. 4,551,433, deBoer et al., *Proc. Nat'l Acad. Sci. USA* (1983) 80:21-25, and Siebenlist et al., *Cell* (1980) 20:269.

Expression systems in yeast include those described in Hinnen et al., *Proc. Nat'l Acad. Sci. USA* (1978) 75:1929; Ito et al., *J. Bacteriol.* (1983) 153:163; Kurtz et al., *Mol. Cell. Biol.* (1986) 6:142; Kunze et al., *J. Basic Microbiol.* (1985) 25:141; Gleeson et al., *J. Gen. Microbiol.* (1986) 132:3459, Roggenkamp et al., *Mol. Gen. Genet.* (1986) 202:302) Das et al., *J. Bacteriol.* (1984) 158:1165; De Louvencourt et al., *J. Bacteriol.* (1983) 154:737, Van den Berg et al., *Bio/Technology* (1990) 8:135; Kunze et al., *J. Basic Microbiol.* (1985) 25:141; Cregg et al., *Mol. Cell. Biol.* (1985) 5:3376, U.S. Pat. No. 4,837,148, U.S. Pat. No. 4,929,555; Beach and Nurse, *Nature* (1981) 300:706; Davidow et al., *Curr. Genet.* (1985) 10:380, Gaillardin et al., *Curr. Genet.* (1985) 10:49, Ballance et al., *Biochem. Biophys. Res. Commun.* (1983) 112:284-289; Tilburn et al., *Gene* (1983) 26:205-221, Yelton et al., *Proc. Nat'l Acad. Sci. USA* (1984) 81:1470-1474, Kelly and Hynes, *EMBO J.* (1985) 4:475479; EP 244,234, and WO 91/00357.

Expression of metastatic marker expression constructs in insects can be carried out as described in U.S. Pat. No. 4,745, 051, Friesen et al. (1986) "The Regulation of Baculovirus Gene Expression" in: THE MOLECULAR BIOLOGY OF BACULOVIRUSES (W. Doerfler, ed.), EP 127,839, EP 155,476, and Vlak et al., *J. Gen. Virol.* (1988) 69:765-776, Miller et al., *Ann. Rev. Microbiol.* (1988) 42:177, Carbonell et al., *Gene* (1988) 73:409, Maeda et al., *Nature* (1985) 315:592-594, Lebacq-Verheyden et al., *Mol. Cell. Biol.* (1988) 8:3129; Smith et al., *Proc. Nat'l Acad. Sci. USA* (1985) 82:8404, Miyajima et al., *Gene* (1987) 58:273; and Martin et al., *DNA* (1988) 7:99. Numerous baculoviral strains and variants and corresponding permissive insect host cells from hosts are described in Luckow et al., *Bio/Technology* (1988) 6:47-55, Miller et al., in GENETIC ENGINEERING (Setlow, J. K. et al. eds.), Vol. 8 (Plenum Publishing, 1986), pp. 277-279, and Maeda et al., *Nature*, (1985) 315:592-594.

Mammalian expression of metastatic marker expression constructs can be achieved as described in Dijkema et al., *EMBO J.* (1985) 4:761, Gorman et al., *Proc. Nat'l Acad. Sci. USA* (1982b) 79:6777, Boshart et al., *Cell* (1985) 41:521 and U.S. Pat. No. 4,399,216. Other features of mammalian expression of metastatic marker expression constructs can be facilitated as described in Ham and Wallace, *Meth. Enz.* (1979) 58:44, Barnes and Sato, *Anal. Biochem.* (1980) 102: 255, U.S. Pat. No. 4,767,704, U.S. Pat. No. 4,657,866, U.S. Pat. No. 4,927,762, U.S. Pat. No. 4,560,655, WO 90/103430, WO 87/00195, and U.S. RE 30,985.

Subgenomic polynucleotides of the invention can also be used in gene delivery vehicles, for the purpose of delivering a metastatic marker mRNA or oligonucleotide (either with the sequence of native metastatic marker mRNA or its complement), full-length metastatic marker protein, metastatic marker fusion protein, metastatic marker polypeptide, or metastatic marker-specific ribozyme or single-chain antibody, into a cell, preferably a eukaryotic cell. According to the present invention, a gene delivery vehicle can be, for example, naked plasmid DNA, a viral expression vector comprising a metastatic marker subgenomic polynucleotide, or a metastatic marker subgenomic polynucleotide in conjunction with a liposome or a condensing agent.

The invention provides a method of detecting metastatic marker gene expression in a biological sample. Detection of metastatic marker gene expression is useful, for example, for identifying metastases or for determining metastatic potential in a tissue sample, preferably a tumor. Appropriate treatment regimens can then be designed for patients who are at risk for developing metastatic cancers in other organs of the body.

The body sample can be, for example, a solid tissue or a fluid sample. The native polypeptide encoded by SEQ ID NO:1 is a putative secreted protein, and is likely to be detected in body fluids including blood and lymphatic fluid, particularly those draining from tumor sites in the body. Protein or nucleic acid expression products can be detected in the body sample. In one embodiment, the body sample is assayed for the presence of a metastatic marker protein. A metastatic marker protein comprises a sequence encoded by a nucleotide sequence shown in SEQ ID NO:1 or its complement and can be detected using the marker protein-specific antibodies of the present invention. The antibodies can be labeled, for example, with a radioactive, fluorescent, biotinylated, or enzymatic tag and detected directly, or can be detected using indirect immunochemical methods, using a labeled secondary antibody. The presence of the metastatic marker proteins can be assayed, for example, in tissue sections by immunocytochemistry, or in lysates, using Western blotting, as is known in the art. Presence of the marker protein is indicative that the tissue sample is metastatic.

In another embodiment, the body sample is assayed for the presence of marker protein mRNA. A sample can be contacted with a nucleic acid hybridization probe capable of hybridizing with the mRNA corresponding the selected polypeptide. Still further, the sample can be subjected to a Northern blotting technique to detect mRNA, indicating expression of the polypeptide. For those techniques in which mRNA is detected, the sample can be subjected to a nucleic acid amplification process whereby the mRNA molecule or a selected part thereof is amplified using appropriate nucleotide primers. Other RNA detection techniques can also be used, including, but not limited to, in situ hybridization.

Marker protein-specific probes can be generated using the cDNA sequence disclosed in SEQ ID NO:1. The probes are preferably at least 15 to 50 nucleotides in length, although they can be at least 8, 10, 11, 12, 20, 25, 30, 35, 40, 45, 60, 75, or 100 or more nucleotides in length. A preferable region for selecting probes is within nucleotide positions 446-1173 of SEQ ID NO:1. The probes can be synthesized chemically or can be generated from longer polynucleotides using restriction enzymes. The probes can be labeled, for example, with a radioactive, biotinylated, or fluorescent tag.

Optionally, the level of a particular metastatic marker expression product in a body sample can be quantitated. Quantitation can be accomplished, for example, by comparing the level of expression product detected in the body sample with the amounts of product present in a standard curve. A comparison can be made visually or using a technique such as densitometry, with or without computerized assistance. For use as controls, body samples can be isolated from other humans, other non-cancerous organs of the patient being tested, or non-metastatic breast cancer from the patient being tested. As indicated by the results herein, expression of SEQ ID NO:1 in low-metastatic or non-metastatic breast cancer cells is between 3% and 44% of the expression levels in highly-metastatic breast cancer cells. If expression in a test sample is at least 2-fold greater than in a suitable control sample, this is indicative of metastatic cells.

Polynucleotides encoding metastatic marker-specific reagents of the invention, such as antibodies and nucleotide probes, can be supplied in a kit for detecting marker gene expression products in a biological sample. The kit can also contain buffers or labeling components, as well as instructions for using the reagents to detect the marker expression products in the biological sample.

Expression of a metastatic marker gene can be altered using an antisense oligonucleotide sequence. The antisense sequence is complementary to at least a portion of the coding sequence (nucleotides 365-1173) of a metastatic marker gene having a nucleotide sequence shown in SEQ ID NO:1. Preferably, the antisense oligonucleotide sequence is at least six nucleotides in length, but can be at least about 8, 12, 15, 20, 25, 30, 35, 40, 45, or 50 nucleotides long. Longer sequences can also be used. Antisense oligonucleotide molecules can be provided in a DNA construct and introduced into cells whose division is to be decreased. Such cells include highly-metastatic breast cancer cells.

Antisense oligonucleotides can comprise deoxyribonucleotides, ribonucleotides, or a combination of both. Oligonucleotides can be synthesized manually or by an automated synthesizer, by covalently linking the 5' end of one nucleotide with the 3' end of another nucleotide with non-phosphodiester internucleotide linkages such alkylphosphonates, phosphorothioates, phosphorodithioates, alkylphosphonothioates, alkylphosphonates, phosphoramidates, phosphate esters, carbamates, acetamidate, carboxymethyl esters, carbonates, and phosphate triesters. See Brown, 1994, *Meth. Mol. Biol.* 20:1-8; Sonveaux, 1994, *Meth. Mol. Biol.* 26:1-72; Uhlmann et al., 1990, *Chem. Rev.* 90:543-583.

Antibodies of the invention which specifically bind to a metastatic marker protein can also be used to alter metastatic marker gene expression. By antibodies is meant antibodies and parts or derivatives thereof, such as single chain antibodies, that retain specific binding for the protein. Specific antibodies bind to metastatic marker proteins and prevent the proteins from functioning in the cell. Polynucleotides encoding specific antibodies of the invention can be introduced into cells, as described above.

Marker proteins of the present invention can be used to screen for drugs which have a therapeutic anti-metastatic effect. The effect of a test compound on metastatic marker protein synthesis can also be used to identify test compounds which modulate metastasis. Test compounds which can be screened include any substances, whether natural products or synthetic, which can be administered to the subject. Libraries or mixtures of compounds can be tested. The compounds or substances can be those for which a pharmaceutical effect is previously known or unknown.

Synthesis of metastatic marker proteins can be measured by any means for measuring protein synthesis known in the art, such as incorporation of labeled amino acids into proteins and detection of labeled metastatic marker proteins in a polyacrylamide gel. The amount of metastatic marker proteins can be detected, for example, using metastatic marker protein-specific antibodies of the invention in Western blots. The amount of the metastatic marker proteins synthesized in the presence or absence of a test compound can be determined by any means known in the art, such as comparison of the amount of metastatic marker protein synthesized with the amount of the metastatic marker proteins present in a standard curve.

The effect of a test compound on metastatic marker protein synthesis can also be measured by Northern blot analysis, by measuring the amount of metastatic marker protein mRNA expression in response to the test compound using metastatic marker protein specific nucleotide probes of the invention, as is known in the art.

Typically, a biological sample is contacted with a range of concentrations of the test compound, such as 1.0 nM, 5.0 nM, 10 nM, 50 nM, 100 nM, 500 nM, 1 mM, 10 mM, 50 mM, and 100 mM. Preferably, the test compound increases or decreases expression of a metastatic marker protein by 60%, 75%, or 80%. More preferably, an increase or decrease of 85%, 90%, 95%, or 98% is achieved.

The invention provides compositions for increasing or decreasing expression of metastatic marker protein. These compositions comprise polynucleotides encoding all or at least a portion of a metastatic marker protein gene expression product. Preferably, the therapeutic composition contains an expression construct comprising a promoter and a polynucleotide segment encoding at least a portion of the metastatic marker protein which is effective to decrease metastatic potential. Portions of metastatic marker genes or proteins which are effective to decrease metastatic potential of a cell can be determined, for example, by introducing portions of metastatic marker genes or polypeptides into metastatic cell lines, such as MDA-MB-231, MDA-MB-435, Km12C, or Km12L4, and assaying the division rate of the cells or the ability of the cells to form metastases when implanted in vivo, as is known in the art. Non-metastatic cell lines, such as MCF-7, can be used to assay the ability of a portion of a metastatic marker protein to increase expression of a metastatic marker gene.

Typically, a therapeutic metastatic marker composition is prepared as an injectable, either as a liquid solution or suspension; however, solid forms suitable for solution in, or suspension in, liquid vehicles prior to injection can also be prepared. A metastatic marker composition can also be formulated into an enteric coated tablet or gel capsule according to known methods in the art, such as those described in U.S. Pat. No. 4,853,230, EP 225,189, AU 9,224,296, and AU 9,230,801.

Administration of the metastatic marker therapeutic agents of the invention can include local or systemic administration, including injection, oral administration, particle gun, or catheterized administration, and topical administration. Various methods can be used to administer a therapeutic metastatic marker composition directly to a specific site in the body.

For treatment of tumors, including metastatic lesions, for example, a therapeutic metastatic marker composition can be injected several times in several different locations within the body of tumor. Alternatively, arteries which serve a tumor can be identified, and a therapeutic composition injected into such an artery, in order to deliver the composition directly into the tumor.

A tumor which has a necrotic center can be aspirated and the composition injected directly into the now empty center of the tumor. A therapeutic metastatic marker composition can be directly administered to the surface of a tumor, for example, by topical application of the composition. X-ray imaging can be used to assist in certain of the above delivery methods. Combination therapeutic agents, including a metastatic marker proteins or polypeptide or a metastatic marker subgenomic polynucleotide and other therapeutic agents, can be administered simultaneously or sequentially.

Alternatively, a metastatic marker therapeutic composition can be introduced into human cells ex vivo, and the cells then replaced into the human. Cells can be removed from a variety of locations including, for example, from a selected tumor or from an affected organ. In addition, a therapeutic composition can be inserted into non-affected cells, for example, dermal fibroblasts or peripheral blood leukocytes. If desired, particular fractions of cells such as a T cell subset or stem cells can also be specifically removed from the blood (see, for example, PCT WO 91/16116). The removed cells can then be contacted with a metastatic marker therapeutic composition utilizing any of the above-described techniques, followed by the return of the cells to the human, preferably to or within the vicinity of a tumor or other site to be treated. The methods described above can additionally comprise the steps of depleting fibroblasts or other non-contaminating tumor cells subsequent to removing tumor cells from a human, and/or the step of inactivating the cells, for example, by irradiation.

Both the dose of a metastatic marker composition and the means of administration can be determined based on the specific qualities of the therapeutic composition, the condition, age, and weight of the patient, the progression of the disease, and other relevant factors. Preferably, a therapeutic composition of the invention decreases expression of the metastatic marker genes by 50%, 60%, 70%, or 80%. Most preferably, expression of the metastatic marker genes is decreased by 90%, 95%, 99%, or 100%. The effectiveness of the mechanism chosen to alter expression of the metastatic marker genes can be assessed using methods well known in the art, such as hybridization of nucleotide probes to mRNA of the metastatic marker genes, quantitative RT-PCR, or detection of the metastatic marker proteins using specific antibodies of the invention.

If the composition contains the metastatic marker proteins, polypeptide, or antibody, effective dosages of the composition are in the range of about 5 µg to about 50 µg/kg of patient body weight, about 50 µg to about 5 mg/kg, about 100 µg to about 500 µg/kg of patient body weight, and about 200 to about 250 µg/kg.

Therapeutic compositions containing metastatic marker subgenomic polynucleotides can be administered in a range of about 100 ng to about 200 mg of DNA for local administration. Concentration ranges of about 500 ng to about 50 mg, about 1 µg to about 2 mg, about 5 µg to about 500 µg, and about 20 µg to about 100 µg of DNA can also be used during a gene therapy protocol. Factors such as method of action and efficacy of transformation and expression are considerations that will affect the dosage required for ultimate efficacy of the metastatic marker subgenomic polynucleotides. Where greater expression is desired over a larger area of tissue, larger amounts of metastatic marker subgenomic polynucleotides or the same amounts readministered in a successive protocol of administrations, or several administrations to different adjacent or close tissue portions of, for example, a tumor site, can be required to effect a positive therapeutic outcome. In all cases, routine experimentation in clinical trials will determine specific ranges for optimal therapeutic effect.

Expression of an endogenous metastatic marker gene in a cell can also be altered by introducing in frame with the endogenous metastatic marker gene a DNA construct comprising a metastatic marker protein targeting sequence, a regulatory sequence, an exon, and an unpaired splice donor site by homologous recombination, such that a homologously recombinant cell comprising the DNA construct is formed. The new transcription unit can be used to turn the metastatic marker gene on or off as desired. This method of affecting endogenous gene expression is taught in U.S. Pat. No. 5,641,670, which is incorporated herein by reference.

A metastatic marker subgenomic polynucleotide can also be delivered to subjects for the purpose of screening test compounds for those which are useful for enhancing transfer of metastatic marker subgenomic polynucleotides to the cell or for enhancing subsequent biological effects of metastatic marker subgenomic polynucleotides within the cell. Such biological effects include hybridization to complementary metastatic marker mRNA and inhibition of its translation, expression of a metastatic marker subgenomic polynucleotide to form metastatic marker mRNA and/or metastatic marker protein, and replication and integration of a metastatic marker subgenomic polynucleotide. The subject can be a cell culture or an animal, preferably a mammal, more preferably a human.

The above disclosure generally describes the present invention. A more complete understanding can be obtained by reference to the following specific examples which are provided herein for purposes of illustration only, and are not intended to limit the scope of the invention.

EXAMPLES

Materials and Methods

Cell culture. MDA-MB-435, MDA-MB-231, ALAB, MDA-MB-468, MDA-MB-361, ZR-75-1, MCF-7, MDA-MB-453 and SK-BR-3 human breast cancer cell lines (obtained from Chiron Master Culture Collection, Chiron Corporation) were grown at 37° C. in 5% $CO_2$ in DMEM+HAM'S F-12 (1:1) (Bio*Whittaker, Walkersville, Md.) containing 2 mM L-Glutamine, 1 mM Sodium Pyruvate, 100 U/ml Penicillin and 100 µg/ml Streptomycin (Bio*Whittaker, Walkersville, Md), 1×Vitamin Solution, 1×Non-Essential Amino Acids (Irvine Scientific, Santa Ana, Calif.), and 10% heat-inactivated fetal bovine serum (Life Technologies, Rockville, Md). COS-7 cells were obtained from ATCC and grown at 37° C. in 5% $CO_2$ in DMEM with 10% heat-inactivated fetal bovine serum (Life Technologies).

Concentration of Opti-MEM1 supernatant. Opti-MEM1 (Life Technologies) culture media were concentrated through Centricon YM-10 and/or Microcon YM-10 columns (Millipore Corporation, Bedford, Mass.). SDS-PAGE sample loading buffer was then added and the samples were boiled.

Northern blot hybridization. Total RNAs were prepared from cultured breast cancer cell lines and tumor tissues of SCID mice transplanted with breast cancer cell lines with RNeasy Maxi Kit (Qiagen, Valencia, Calif.). Approximately 20 µg of total RNA per lane was loaded onto a formaldehyde/agarose gel for electrophoresis, then transferred to a Hybond-N+nylon membrane (Amersham Life Science, Little Chalfont, England). The blot was fixed by UV irradiation. Rapid-Hyb buffer (Amersham Life Science) with 5 mg/ml denatured single stranded sperm DNA was pre-warmed to 65° C. and the blot was pre-hybridized in the buffer with shaking at 65° C. for 30 minutes. A hsOAF cDNA fragment or a β-actin cDNA fragment as probe labeled with $[\alpha\text{-}^{32}P]dCTP$ (3000 Ci/mmol, Amersham Pharmacia Biotech Inc., Piscataway, N.J.) (Prime-It RmT Kit, Stratagene, La Jolla, Calif.) and purified with ProbeQuant™ G-50 Micro Column (Amersham Pharmacia Biotech Inc.) was added and hybridized to the blot with shaking at 65° C. for overnight. The blot was washed in 2×SSC, 0.1%(w/v) SDS at room temperature for 20 minutes, twice in 1×SSC, 0.1%(w/v) SDS at 65° C. for 15 minutes, then exposed to Hyperfilms (Amersham Life Science).

Immunoblotting. Protein samples were subjected to electrophoresis on 10-20% SDS-PAGE gels then transferred to PVDF membranes (0.2 µm) by electroblotting in 25 mM Tris, 192 mM glycine, 20% (v/v) methanol, pH 8.3. Membranes were blocked in TBST (pH 7.5) containing 10% non-fat milk, then blotted in PBS (pH 7.4) containing 1% BSA with a rabbit anti-hsOAF serum (1:1000), followed by probing with a secondary antibody alkaline phosphatase-conjugated goat anti-rabbit IgG (1:2000) (Santa Cruz Biotechnology, Inc., Santa Cruz, Calif. ). Protein bands were then visualized by NBT/BCIP reagent (Boehringer Mannheim, Germany).

Transient transfection. The coding region (356-1174) of hsOAF cDNA was cloned into a modified expression vector pRetro-On (Clontech, Palo Alto, Calif.). The pRetro-On vector harboring hsOAF or the control pRetro-On vector with GFP was transfected into COS-7 cells on a 100 mm culture plate using Effectene™ Transfection Reagent Kit (Qiagen) as instructed in the protocol provided by the manufacturer. Cells were recovered in DMEM with 10% FBS for overnight then switched to Opti-MEM1. After two more days, the supernatant was collected and concentrated for western blot analysis.

Antisense oligo transfection. MDA-MB-435 cells were seeded on 6-well culture plates one day before transfection to yield a 90% density at transfection. 100 µM antisense or reverse control oligo was diluted to 2 µM in Opti-MEM1 for transfection. 0.5 mM sterile lipitoid1 was diluted to a ratio of 1.5 nmol lipitoid1: 1 µg oligo in the same volume of Opti-MEM1. The diluted oligo and the diluted lipitoid1 were mixed and immediately added to cells in culture media to a final concentration of 100, 200, or 300 nM oligo. After 6 hrs, the transfection mixture was replaced with normal culture media and cells were incubated for recovery for overnight. The sequence of the antisense oligo is AGCTGCGGATGC-CACACTTGTAGG (SEQ ID NO:4) and the sequence of the reverse control oligo is GGATGTTCACACCGTAG-GCGTCGA (SEQ ID NO:5).

Matrigel invasion assay. Cells were trypsinized, washed, and resuspended in media for counting. $4 \times 10^4$ cells were washed and resuspended in 100 µl media on ice. 200 µl Matrigel (Collaborative Biomedical Products, Bedford, Mass.) was added to the cells on ice. The Matrigel and the cells were carefully mixed then dispensed into a well of 24-well culture plate and solidified at 37° C. for 30 min. The Matrigel-cell mixture was topped with 0.5 ml medium and incubated at 37° C. in 5% $CO_2$ for 6 days. The medium was replenished every 2 days.

Proliferation assay. Cells were trypsinized, washed, and resuspended in media for counting. Cells were then transferred into 96-well plates (5000 cells/well) for incubation. Cell numbers were measured with Quantos™ Cell Proliferation Assay Kit (Stratagene, La Jolla, Calif.) every day.

Example 1

Identification of a Human cDNA Sequence

DNA encoding a putative human homologue of the Drosophila Out at First (oaf) gene is shown in SEQ ID NO:1. An alignment of hsOAF and *Drosophilia* OAF is shown in FIG. 7. The polynucleotide comprises 2366 base pairs, and an open reading frame is identified. A translation of the ORF, a polypeptide of 273 amino acids, is shown in SEQ ID NO:2. FIG. 4 provides the DNA and amino acid sequences, indicating the position of the ORF. The first 30 amino acids form a signal peptide, indicating that the protein may be secreted. The amino acid sequence of the signal peptide is: MRLPGVPLARPALLLLLPLLAPLLG#TGAPA (SEQ ID NO:3). "#" indicates the location of the predicted protease cut site.

Example 2

Differential Expression of SEQ ID NO:1 In Breast Cancer Cell Lines

Expression of SEQ ID NO:1 in the following human breast cancer cell lines was compared:
MDA-MB-361, derived from human breast adenocarcinoma;
MDA-MB-231, derived from human breast cancer cells metastatic to bone and/or lung;
MDA-MB-468, derived from estrogen receptor-negative human breast cancer cells;
MDA-MB-435, derived from estrogen receptor-negative human breast carcinoma cells;
MCF-7, derived from non-metastatic human breast cancer cells; and
ZR-75-1, derived from estrogen receptor-positive human breast carcinoma cells.

Expression of SEQ ID NO:1 was measured in the highly metastatic breast cancer cell lines MDA-MB 231 and MDA-MB-435, and compared with low-metastatic or non-metastatic breast cancer cell lines. Expression in MDA-MB-361 was 11% of the level in MDA-MB-231; expression in MDA-MD-468 was 44% of the level in MDA-MB-231; expression in MCF-7 was 17% of the level in MDA-MB-231; and expression in ZR-75-1 was 12% of the level in MDA-MB-231.

Expression in MDA-MB-361 was 6% of the level in MDA-MB-435; expression in MDA-MB-468 was 36% of the level in MDA-MB-435; and expression in MCF-7 was 3% of the level in MDA-MB-435. Thus, as shown in Table 2, there is a clear trend of increased expression of SEQ ID NO:1 in breast cancer cell lines derived from human tumors with high metastatic potential.

TABLE 2

| High Metastatic Cell Line | Low Metastatic Cell Lines: % Expression Relative to High Metastatic Cell Line | | | |
|---|---|---|---|---|
| | MDA-MB-361 | MDA-MB-468 | MCF-7 | ZR-75-1 |
| MDA-MB-231 | 11% | 44% | 17% | 12% |
| MDA-MB-435 | 6% | 36% | 3% | ND |

Figure 6:
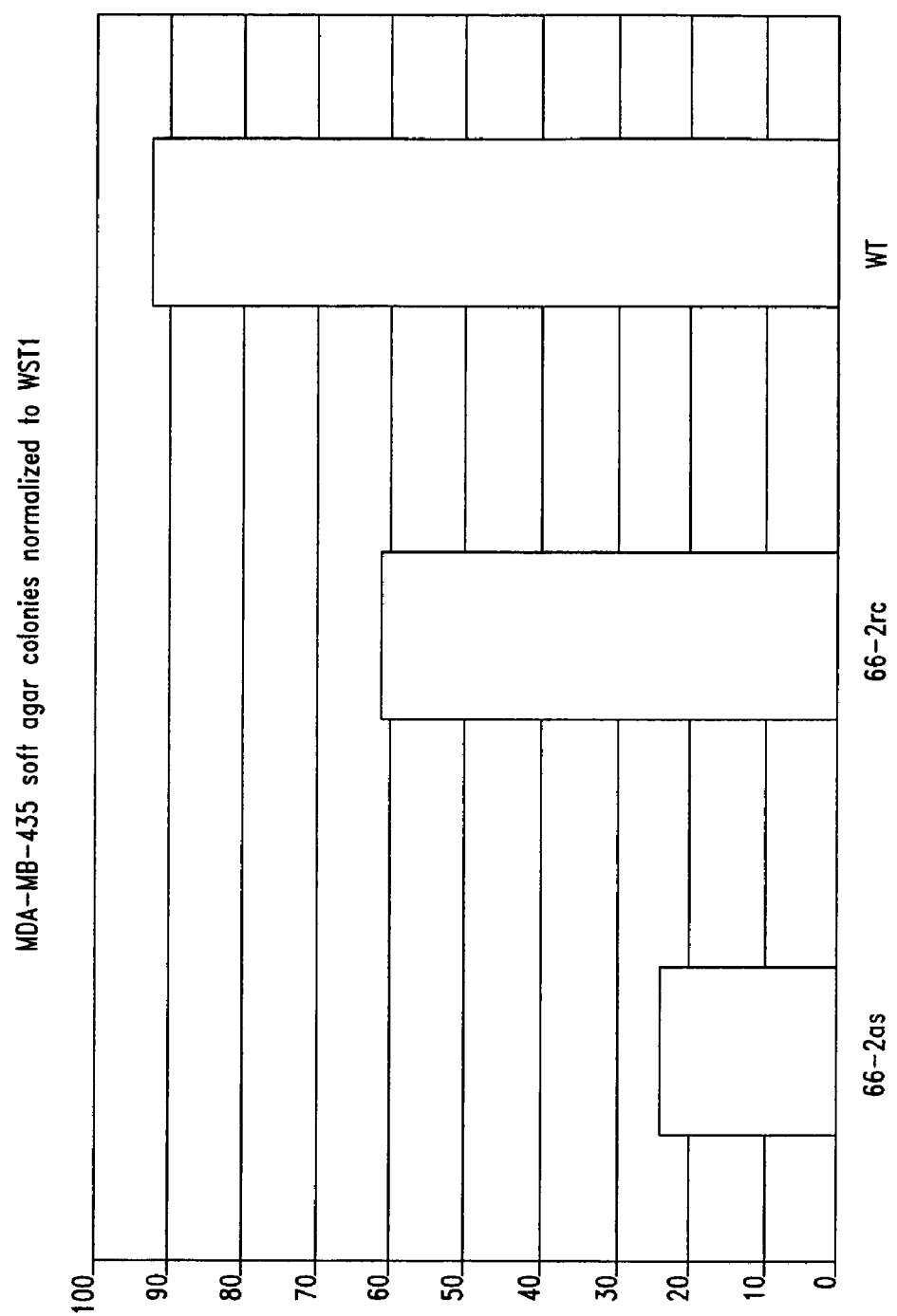
FIG. 6 illustrates the growth of colonies by MDA-MB-435 cells in soft agar following treatment with antisense oligo SEQ ID NO:4 (66-2as) or reverse control SEQ ID NO:5 (66-2rc), relative to untreated cells (WT).

A similar expression pattern of this gene remained in tumor tissue samples from SCID mice transplanted with tumorigenic mammary carcinoma cell lines. (FIG. 6.)

Figure 8A:
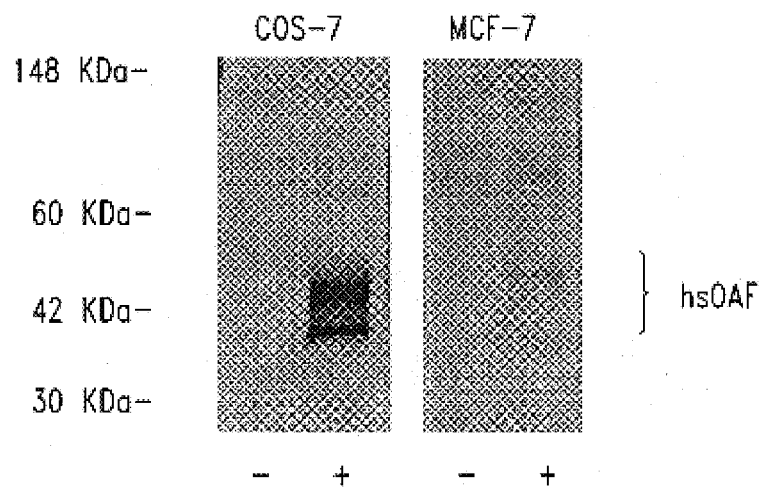
FIG. 8A illustrates the expression of hsOAF protein in COS-7 and MCF-7 cell lines.
Figure 8B:
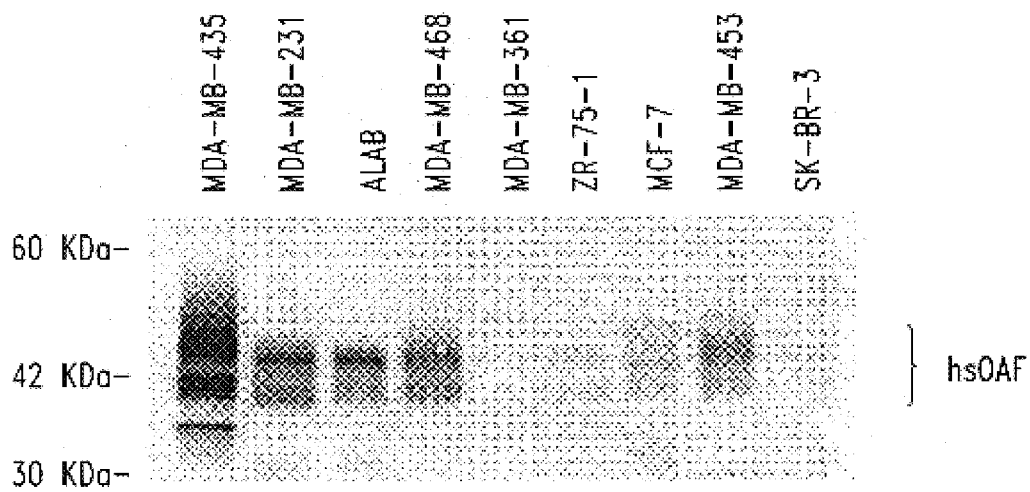
FIG. 8B illustrates the expression of hsOAF protein in mammory carcinoma cell lines.

Example 3 hsOAF Encodes a Secreted Protein and hsOAF Protein Secretion Levels are Consistent with hsOAF mRNA Expression Levels of Mammary Carcinoma Cell Lines A predicted signal peptide sequence is located at the N-terminus of the deduced amino acid sequence of hsOAF gene (FIG. 3). To verify the secretion of hsOAF protein, transient transfection of COS-7 cells and MCF-7 cells was performed with vector pRetro-On harboring hsOAF cDNA. Meanwhile, vector pRetro-On harboring GFP was used as control. Using a hsOAF rabbit antiserum, secreted hsOAF protein was detected in Opti-MEM1 culture media of both cell lines after transfection with hsOAF by immunoblotting (FIG. 8A). Secreted hsOAF protein was probably glycosylated since multiple bands with higher apparent molecular weights were seen (the predicted MW of secreted hsOAF protein is 28 Kda). The same hsOAF antiserum was used to detect the secretion of hsOAF protein by various mammary carcinoma cell lines. The secretion levels of hsOAF protein were consistent with the hsOAF mRNA expression levels among these cell lines overall: highly metastatic cell lines showed much stronger hsOAF secretion than low metastatic/nonmetastatic cell lines (FIG. 8B). MDA-MB-435 had the strongest hsOAF protein secretion.

Example 4

Figure 12A:
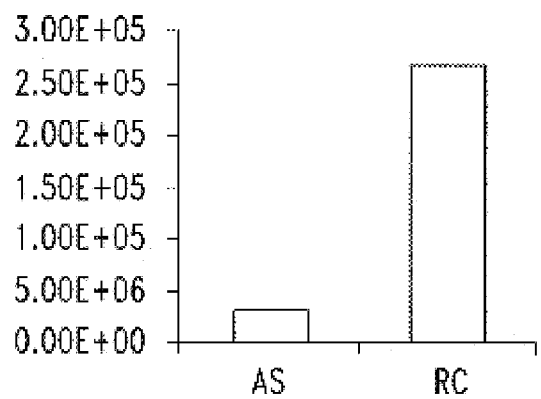
FIGS. 12A and 12B illustrate the secretion of hsOAF by MDA-MB-435 cells treated with antisense oligo (SEQ ID NO:4) or reverse control oligo (SEQ ID NO:5).
Figure 12B:
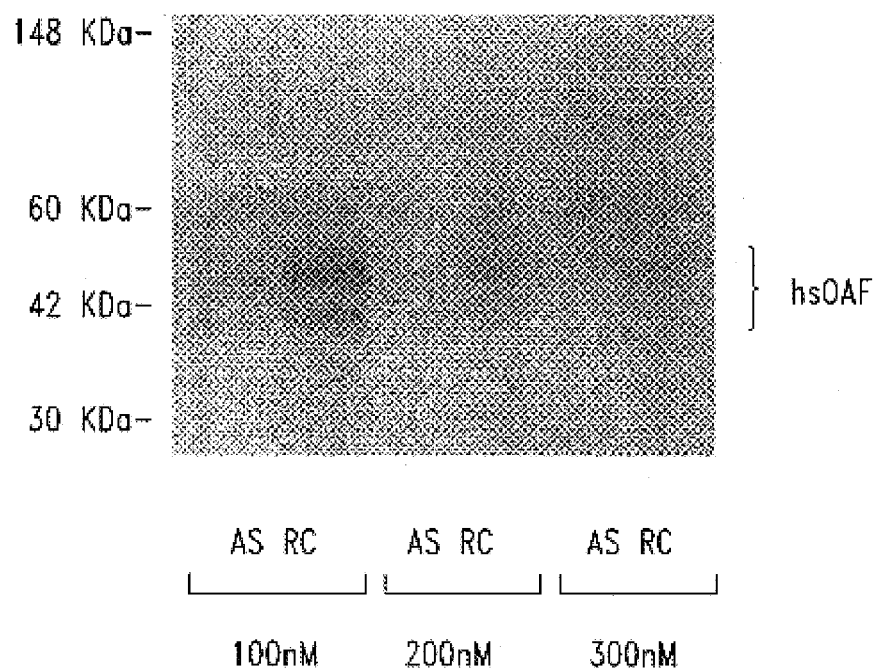

Knockout of hsOAF Expression in MDA-MB-435 Cells by Antisense Oligo Caused Morphological Change, Reduced Cell Invasiveness and Slower Proliferation Rate To determine if high level of hsOAF gene expression is essential for the metastatic potential of human mammary carcinoma cells, antisense oligo technology was used to knock out hsOAF expression, then the consequent effects were observed. MDA-MB-435 was chosen since this highly metastatic cell line showed the strongest hsOAF protein secretion among all of the breast cancer cell lines examined. Several pairs of hsOAF antisense (AS) and reverse control (RC) oligos were chosen to test for their ability to shut down hsOAF gene expression at the mRNA level. Real-time quantitative RT-PCR analysis in Lightcycler (Roche Diagnostics, Indianapolis, Ind.) was performed to measure hsOAF mRNA levels in cells. Kang, S. et al., *Cancer Research* 60(18):5296-5302 (2000). The best pair was then selected for the titration of oligo working concentration. Low oligo concentration is preferred to reduce potential oligo toxicity to cells. The results indicated that treatment with 100 nM of the antisense oligo was sufficient to significantly reduce hsOAF protein secretion of MDA-MB-435 cells. (FIG. 12). This pair of oligos (SEQ ID NO:4 (AS) and 5 (RC)) at 100 nM working concentration was used for all the following experiments.

After treatment of MDA-MB-435 cells with hsOAF antisense oligo, dramatic morphological alteration of cells was observed along with reduced hsOAF protein secretion (FIG. 10A). Cells became more spherical and lost their spreading protrusions. Meanwhile, cells treated with reverse control oligo remained similar to the normal tissue cultured MDA-MB-435 cells. Furthermore, culture medium of normal MDA-MB-435 cells containing high level of hsOAF protein as the conditioned medium added to cells treated with antisense oligo was able to prevent this morphological change, though not completely. This alteration of cell shape may be an indication of reduced invasion ability of cells.

Matrigel invasion assay was then performed to estimate the invasiveness of cells. It has been reported that a stellate, invasive morphology of breast cancer cells embedded in matrigel correlates with their metastatic potential (Thompson, E. W., et al., *J. Cell Physiol.* 150(3):534-44 (1992); Sugiura, T., et al. *J. Cell Biol*, 146(6):1375-89 (1999); Albini, A., et al., *Cancer Res.* 47(f2):3239-45 (1987); and Kramer, R. H., et al., *Cancer Res.* 46(4 Pt 2):1980-89 (1986)) and this was confirmed with various breast cancer cell lines grown in matrigel. Cells were trypsinized, counted, and mixed with matrigel. Media were then topped on the cell-matrigel mixture. After 6 days of incubation, cell invasion was examined (FIG. 10B). The results showed that cells treated with hsOAF reverse control oligo formed penetrating, invasive, network-like three-dimensional structures, as the normal MDA-MB-435 cells did; on the other hand, cells treated with hsOAF antisense oligo only formed smooth, spherical colonies. Again, penetrating colonies were also observed in hsOAF antisense oligo-treated cells incubated in the conditional medium. These data demonstrate that secreted hsOAF protein is required for the invasiveness and metastatic potential of MDA-MB-435 cells.

Additional experiments were performed to examine if secreted hsOAF protein was involved in MDA-MB-435 cell growth. Cell proliferation assay results indicated that knockout of hsOAF protein secretion indeed slowed down proliferation rate of MDA-MB-435 cells, though the change was moderate.

Example 5

Figure 9:
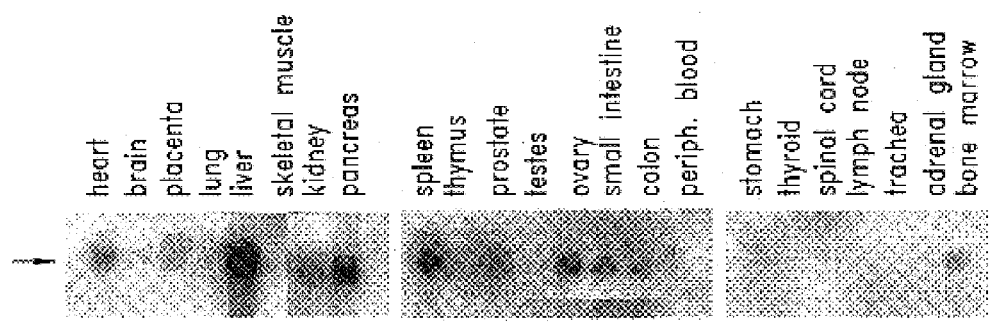
FIG. 9 illustrates the expression of hsOAF in normal human tissues.

Northern Blot Analysis of RNA Expression in Human Breast Cancer Cell Lines and in Human Tissues As shown in FIG. 5, mRNA expression was upregulated in metastatic cell lines MDA-MB-231 and MDA-MB-435. Total RNA was prepared using the RNeasy Kit from Quiagen. Northern blot analysis was performed using 20-30 μg total RNA isolated by guanidinium thiocyanate/phenol chloroform extraction from cell lines, from primary tumors, or from metastases in lung. Primary tumors and lung metastasis were developed from cell lines injected into scid mice according to methods well known in the art. Plasmids containing partial cDNA clones of hOAF cloned into pCR2.0-TA Vector (In vitrogen) were radiolabeled and hybridized at 65° C. in Express-hyb (Clontech). Among all the tissues examined, liver, pancreas, spleen, ovary and small intestine showed significant hsOAF expression. HsOAF mRNA expression was also detected in heart, skeletal muscle, kidney, prostate, colon and bone marrow. (FIG. 9).

Table 3 shows the percentage of hsOAF positives in a variety of tumors and normal tissues.

TABLE 3

| Immunohistochemistry: Percentage of hsOAF positives | | |
|---|---|---|
| | Tumor | Normal |
| Pancreas | 9/11 | 0/9 |
| Esophagus | 5/8 | 0/1 |
| Liver | 3/6 | 0/13 |
| Stomach | 6/7 | 6/10 |
| Breast | 1/1 | |
| Hodgkin's | 1/8 | |

Example 6

Soft Agar Assay

Soft Agar Assay: The bottom layer consisted of 2 ml of 0.6% agar in media plated fresh within a few hours of layering on the cells. For the cell layer, MDA-MB-435 cells as described above were removed from the plate in 0.05% trypsin and washed twice in media. Cells were counted in coulter counter, and resuspended to 106 per ml in media. 10 ml aliquots were placed with media in 96-well plates (to check counting with WST1), or diluted further for soft agar assay. 2000 cells were diluted in 800 ml 0.4% agar in duplicate wells above 0.6% agar bottom layer.

Media layer: After the cell layer agar solidified, 2 ml of media was bled on top and antisense or reverse control oligo was added without delivery vehicles. Fresh media and oligos were added every 3-4 days.

Colonies were counted in 10 days to 3 weeks. Fields of colonies were counted by eye. Wst-1 metabolism values were used to compensate for small differences in starting cell number. Larger fields can be scanned for visual record of differences. The results are shown in FIG. 6, in which MDA-MB-435 cells treated with antisense formed fewer colonies compared to cells exposed to the control oligonucleotide.

Those skilled in the art will recognize, or be able to ascertain, using not more than routine experimentation, many equivalents to the specific embodiments of the invention described herein. Such specific embodiments and equivalents are intended to be encompassed by the following claims.

All patents, published patent applications, and publications cited herein are incorporated by reference as if set forth fully herein.

We claim:

1. An isolated nucleic acid molecule comprising a polynucleotide selected from the group consisting of:
   (a) a polynucleotide encoding amino acids from 1 to 273 of SEQ ID NO:2;
   (b) a polynucleotide encoding amino acids from 2 to 273 of SEQ ID NO:2;
   (c) a polynucleotide encoding amino acids from 26 to 273 of SEQ ID NO:2; and
   (d) the polynucleotide complement of the complete polynucleotide of (a), (b), or (c).

2. An isolated nucleic acid molecule comprising a polynucleotide encoding a polypeptide wherein, except for no more than 5 conservative amino acid substitutions, said polypeptide has an amino acid sequence selected from the group consisting of:
   (a) amino acids 1 to 273 of SEQ ID NO:2;
   (b) amino acids 2 to 273 of SEQ ID NO:2; and
   (c) amino acids 26 to 273 of SEQ ID NO:2.

3. The isolated nucleic acid molecule of claim 1, which is DNA.

4. A method of making a recombinant vector comprising inserting a nucleic acid molecule of claim 1(a), (b), or (c), into a vector in operable linkage to a promoter.

5. A recombinant vector produced by the method of claim 4.

6. A method of making a recombinant host cell comprising introducing the recombinant vector of claim 5 into a host cell.

7. A recombinant host cell produced by the method of claim 6.

8. A recombinant method of producing a polypeptide, comprising culturing the recombinant host cell of claim 7 under conditions such that said polypeptide is expressed and recovering said polypeptide.

9. An isolated nucleic acid molecule comprising a polynucleotide at least 95% identical to a polynucleotide selected from the group consisting of:
   (a) a polynucleotide encoding amino acids from 1 to 273 of SEQ ID NO:2;
   (b) a polynucleotide encoding amino acids from 2 to 273 of SEQ ID NO:2;
   (c) a polynucleotide encoding amino acids from 26 to 273 of SEQ ID NO:2; and
   (d) the full polynucleotide complement of the complete polynucleotide of (a), (b), or (c).

10. The isolated nucleic acid molecule of claim 9 wherein the polynucleotide is at least 98% identical to the polynucleotide of (a)-(d).

11. A method of making a recombinant vector comprising inserting a nucleic acid molecule of claim 9 into a vector in operable linkage to a promoter.

12. An isolated nucleic acid molecule comprising a polynucleotide encoding a polypeptide at least 95% identical to SEQ ID NO:2, or the full complement of the complete polynucleotide.

13. The isolated nucleic acid molecule of claim 12 wherein the polynucleotide encodes a polypeptide at least 98% identical to SEQ ID NO:2.

14. The isolated nucleic acid molecule of any one of claims 2, 9 or 12 wherein the polynucleotide is at least 95% identical to SEQ ID NO:1.

15. The isolated nucleic acid molecule of any one of claims 2, 9 or 12 wherein the polynucleotide is at least 98% identical to SEQ ID NO:1.

16. The isolated nucleic acid molecule of claim 2 wherein the polynucleotide encodes a polypeptide wherein, except for no more than 3 conservative amino acid substitutions, said polypeptide has an amino acid sequence selected from the group consisting of:
   (a) amino acids 1 to 273 of SEQ ID NO:2;
   (b) amino acids 2 to 273 of SEQ ID NO:2; and
   (c) amino acids 26 to 273 of SEQ ID NO:2.

17. The isolated nucleic acid molecule of any one of claims 2, 9 or 12 wherein the nucleic acid molecule encodes a polypeptide comprising SEQ ID NO:10.

18. The isolated nucleic acid molecule of any one of claims 2, 9 or 12 wherein the nucleic acid molecule encodes a polypeptide comprising SEQ ID NO:3.

19. The isolated nucleic acid molecule of claim 2 comprising a polynucleotide encoding a polypeptide having no more than 5 conservative amino acid substitutions, wherein the conservative substitutions are selected from the group consisting of:
   (a) leucine to isoleucine;
   (b) leucine to valine;
   (c) aspartate to glutamate; and
   (d) threonine to serine.

* * * * *

UNITED STATES PATENT AND TRADEMARK OFFICE
CERTIFICATE OF CORRECTION

PATENT NO. : 7,605,246 B2
APPLICATION NO. : 09/758575
DATED : October 20, 2009
INVENTOR(S) : Kaufmann et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1390 days.

Signed and Sealed this

Fifth Day of October, 2010

David J. Kappos
*Director of the United States Patent and Trademark Office*

SEQUENCE LISTING

<160> NUMBER OF SEQ ID NOS: 10

<210> SEQ ID NO 1
<211> LENGTH: 2366
<212> TYPE: DNA
<213> ORGANISM: Homo sapiens

<400> SEQUENCE: 1

```
ccgcgaggtg cgcggtctct ttaaggcggg tcctggtggt ttctgtttcc tgaaggaagt      60
gacggggggt gggattgaat gaaaagtgca aaacacaggc tcgcagcgct ggagcccggg     120
gccgcggagc cgggccgggg cagcgccgtc tccgcctcgg gccgccgggg ggcgccctgc     180
tgagcgctac ccacgtgcgt ccgcgccacc tcgcgggcga ccccgcggcc aaggcccccg     240
gcggagcggc tccgggcgc cccgaactag ccccaactt tgggcgaagt ttgcctgcgc       300
ctctccccgc ccccacgcgg cgcgccgggg ccgcggacgg cagcggcccc cggggatgcg     360
ccttcccggg gtaccctgg cgcgccctgc gctgctgctg ctgctgccgc tgctcgcgcc      420
gctgctggga acgggtgcgc cggccgagct gcgggtccgc gtgcggctgc cggacggcca     480
ggtgaccgag gagagcctgc aggcggacag cgacgcggac agcatcagcc tcgagctgcg     540
caagcccgac ggcacccctcg tctccttcac cgccgacttc aagaaggatg tgaaggtctt    600
ccgggccctg atcctggggg agctggagaa ggggcagagt cagttccagg ccctctgctt     660
tgtcacccag ctgcagcaca atgagatcat ccccagtgag gccatggcca agctccggca    720
gaaaaatccc cgggcagtgc ggcaggcgga ggaggttcgg ggtctggagc atctgcacat    780
ggatgtcgct gtcaacttca gccaggggc cctgctgagc ccccatctcc acaacgtgtg      840
tgccgaggcc gtggatgcca tctacacccg ccaggaggat gtccggttct ggctggagca    900
aggtgtggac agttctgtgt tcgaggctct gcccaaggcc tcagagcagg cggagctgcc    960
tcgctgcagg caggtggggg accgcgggaa gccctgcgtc tgccactatg gcctgagcct   1020
ggcctggtac ccctgcatgc tcaagtactg ccacagccgc gaccggccca cgccctacaa   1080
gtgtggcatc cgcagctgcc agaagagcta cagcttcgac ttctacgtgc cccagaggca   1140
gctgtgtctc tgggatgagg atccctaccc aggctagggt gggagcaacc tgggcgggtg   1200
gctgctctgg gcccactgct cttcaccagc cactagaggg ggtggcaacc cccacctgag   1260
gccttatttc cctccctccc cactcccctg gcccctagagc ctgggcccct ctggcccat    1320 ctcacatgac tgtgaagggg gtgtggcatg gcagggggtc tcatgaaggc accccccattc   1380 ccaccctgtg ccttccttgc gggcagagag ggagagaagg gctccccaga tctacacccc   1440
tccctcctgc atctcccctg gagtgttcac ttgcaagctg ccaaaacatg atggcctctg   1500
gttgttctgt tgaactcctt gaacgtttag accctaaaag gagtctatac ctggacaccc   1560
acctccccag acacaactcc cttccccatg cacacatctg gaaggagctg gcccctcagt   1620
cccttcctac tccccaacaa ggggctcact atccccaaag aaggagctgt ggggacccca   1680
cgacgcagcc cctgtactgg attacagcat attctcatct ctggccccga ggctgcctgt   1740
ggggcgagtg gagacctccc atcactgaga cagatcacag accacgagtg cctttcccgg   1800
acctggacgt tgcctccaaa acaggcacca gctctttccc tctctagaca gaaatatttt   1860
tgtaaggttc tggggcaggg agggagcatg aagtacgagg aaaacttgaa ttccagattt   1920
ttaatgcaaa gtatttatca tttctaccag aaataaacgt tttaagtttt tacttgacta   1980
atgagaccca gagtttggag aaaacttttg gccaatgctg ccacctgatg tcagaaagtg   2040
tccccacacc ctagcagtgg cctatcttgg aacaagaact tcgaaagcac ctactgtgtg   2100
ctcagccatt tgaggaagga aggagggaa ggaagatgtt actagggaag gatgagataa    2160
aacttctgca cccaagacaa tgagacagac ataactgcaa ccgtagtaag ccagtcagaa   2220
atagccagcg cgaaggcaag agatggggtg gagattggaa cccgcttca gatctgggct    2280 cggctactta cctgctgtgc agccatgggt caagttgctt gacctctctg tgcctccact   2340
```
cccttagcta taaaatgagc ttactt                                2366

<210> SEQ ID NO 2
<211> LENGTH: 273
<212> TYPE: PRT
<213> ORGANISM: Homo sapiens

<400> SEQUENCE: 2

Met Arg Leu Pro Gly Val Pro Leu Ala Arg Pro Ala Leu Leu Leu Leu
1               5                   10                  15

Leu Pro Leu Leu Ala Pro Leu Leu Gly Thr Gly Ala Pro Ala Glu Leu
            20                  25                  30

Arg Val Arg Val Arg Leu Pro Asp Gly Gln Val Thr Glu Glu Ser Leu
        35                  40                  45

Gln Ala Asp Ser Asp Ala Asp Ser Ile Ser Leu Glu Leu Arg Lys Pro
    50                  55                  60

Asp Gly Thr Leu Val Ser Phe Thr Ala Asp Phe Lys Lys Asp Val Lys
65                  70                  75                  80

Val Phe Arg Ala Leu Ile Leu Gly Glu Leu Lys Gly Gln Ser Gln
                85                  90                  95

Phe Gln Ala Leu Cys Phe Val Thr Gln Leu Gln His Asn Glu Ile Ile
            100                 105                 110

Pro Ser Glu Ala Met Ala Lys Leu Arg Gln Lys Asn Pro Arg Ala Val
        115                 120                 125

Arg Gln Ala Glu Glu Val Arg Gly Leu Glu His Leu His Met Asp Val
    130                 135                 140

Ala Val Asn Phe Ser Gln Gly Ala Leu Leu Ser Pro His Leu His Asn
145                 150                 155                 160

Val Cys Ala Glu Ala Val Asp Ala Ile Tyr Thr Arg Gln Glu Asp Val
                165                 170                 175

Arg Phe Trp Leu Glu Gln Gly Val Asp Ser Ser Val Phe Glu Ala Leu
            180                 185                 190

Pro Lys Ala Ser Glu Gln Ala Glu Leu Pro Arg Cys Arg Gln Val Gly
        195                 200                 205

Asp Arg Gly Lys Pro Cys Val Cys His Tyr Gly Leu Ser Leu Ala Trp
    210                 215                 220

Tyr Pro Cys Met Leu Lys Tyr Cys His Ser Arg Asp Arg Pro Thr Pro
225                 230                 235                 240

Tyr Lys Cys Gly Ile Arg Ser Cys Gln Lys Ser Tyr Ser Phe Asp Phe
                245                 250                 255

Tyr Val Pro Gln Arg Gln Leu Cys Leu Trp Asp Glu Asp Pro Tyr Pro
            260                 265                 270

Gly

<210> SEQ ID NO 3
<211> LENGTH: 30
<212> TYPE: PRT
<213> ORGANISM: Artificial Sequence
<220> FEATURE:
<223> OTHER INFORMATION: Putative signal peptide

<400> SEQUENCE: 3

Met Arg Leu Pro Gly Val Pro Leu Ala Arg Pro Ala Leu Leu Leu Leu
1               5                   10                  15

Leu Pro Leu Leu Ala Pro Leu Leu Gly Thr Gly Ala Pro Ala
            20                  25                  30

-continued

```
<210> SEQ ID NO 4
<211> LENGTH: 24
<212> TYPE: DNA
<213> ORGANISM: Artificial Sequence
<220> FEATURE:
<223> OTHER INFORMATION: Anti-sense oligonucleotide

<400> SEQUENCE: 4
agctgcggat gccacacttg tagg                                              24

<210> SEQ ID NO 5
<211> LENGTH: 24
<212> TYPE: DNA
<213> ORGANISM: Artificial Sequence
<220> FEATURE:
<223> OTHER INFORMATION: Reverse control oligonucleotide

<400> SEQUENCE: 5
ggatgttcac accgtaggcg tcga                                              24

<210> SEQ ID NO 6
<211> LENGTH: 273
<212> TYPE: PRT
<213> ORGANISM: Homo sapiens

<400> SEQUENCE: 6
```

Met Arg Leu Pro Gly Val Pro Leu Ala Arg Pro Ala Leu Leu Leu Leu
1               5                   10                  15

Leu Pro Leu Leu Ala Pro Leu Leu Gly Thr Gly Ala Pro Ala Glu Leu
            20                  25                  30

Arg Val Arg Val Arg Leu Pro Asp Gly Gln Val Thr Glu Glu Ser Leu
        35                  40                  45

Gln Ala Asp Ser Asp Ala Asp Ser Ile Ser Leu Glu Leu Arg Lys Pro
    50                  55                  60

Asp Gly Ile Leu Val Ser Phe Thr Ala Asp Ile Lys Lys Asp Val Lys
65                  70                  75                  80

Val Phe Arg Ala Leu Ile Leu Gly Glu Leu Lys Lys Gly Gln Ser Gln
                85                  90                  95

Phe Gln Ala Leu Cys Phe Val Thr Gln Leu Gln His Asn Glu Ile Ile
            100                 105                 110

Pro Ser Glu Ala Met Ala Lys Leu Arg Gln Lys Asn Pro Arg Ala Val
        115                 120                 125

Arg Gln Ala Glu Glu Val Arg Gly Leu Glu His Leu His Met Asp Val
    130                 135                 140

Ala Val Asn Phe Ser Gln Gly Ala Leu Leu Ser Pro His Leu His Asn
145                 150                 155                 160

Val Cys Ala Glu Ala Val Asp Ala Ile Val Thr Arg Gln Glu Asp Val
                165                 170                 175

Arg Phe Trp Leu Glu Gln Gly Val Asp Ser Ser Val Phe Lys Ala Leu
            180                 185                 190

Pro Lys Ala Ser Glu Gln Ala Glu Leu Pro Arg Cys Arg Gln Val Gly
        195                 200                 205

Asp Arg Gly Lys Pro Cys Val Cys His Tyr Gly Leu Ser Leu Ala Trp
    210                 215                 220

Val Pro Cys Met Leu Lys Val Cys His Ser Arg Asp Arg Pro Thr Pro
225                 230                 235                 240

Val Lys Cys Gly Ile Arg Ser Cys Gln Lys Ser Tyr Ser Phe Asp Phe
                245                 250                 255

```
Val Val Pro Gln Arg Gln Leu Cys Leu Trp Asp Glu Asp Pro Tyr Pro
        260                 265                 270
Gly

<210> SEQ ID NO 7
<211> LENGTH: 332
<212> TYPE: PRT
<213> ORGANISM: Drosphilia melanogaster

<400> SEQUENCE: 7

Met Ile Leu Lys Glu Glu His Pro His Gln Ser Ile Glu Thr Ala Ala
  1               5                  10                  15

Asn Ala Ala Arg Gln Ala Gln Val Arg Trp Arg Met Ala His Leu Lys
             20                  25                  30

Ala Leu Ser Arg Thr Arg Thr Pro Ala His Gly Asn Cys Cys Gly Arg
         35                  40                  45

Val Val Ser Lys Asn His Phe Phe Lys His Ser Arg Ala Phe Leu Trp
     50                  55                  60

Phe Leu Leu Cys Asn Leu Val Met Asn Ala Asp Ala Phe Ala His Ser
 65                  70                  75                  80

Gln Leu Leu Ile Asn Val Gln Asn Gly Gly Glu Val Ile Gln Glu
                 85                  90                  95

Ser Ile Thr Ser Asn Ile Gly Glu Asp Leu Ile Thr Leu Glu Phe Gln
                100                 105                 110

Lys Thr Asp Gly Ile Leu Ile Thr Gln Val Ile Asp Ile Arg Asn Glu
            115                 120                 125

Val Gln Ile Leu Lys Ala Leu Val Leu Gly Glu Glu Lys Arg Gly Gln
        130                 135                 140

Ser Gln Tyr Gln Val Met Cys Phe Ala Thr Lys Phe Asn Lys Gly Asp
145                 150                 155                 160

Phe Ile Ser Ser Ala Ala Met Ala Lys Leu Arg Gln Lys Asn Pro His
                165                 170                 175

Thr Ile Arg Thr Pro Glu Glu Asp Lys Gly Arg Glu Thr Phe Thr Met
            180                 185                 190

Ser Ser Trp Val Gln Leu Asn Arg Ser Leu Pro Ile Thr Arg His Leu
        195                 200                 205

Gln Gly Leu Cys Ala Glu Ala Met Asp Ala Thr Val Val Arg Asp Val
    210                 215                 220

Asp Leu Lys Ala Trp Ala Glu Leu Pro Gly Ser Ser Ile Ser Ser Leu
225                 230                 235                 240

Lys Ala Ala Thr Glu Lys Phe Pro Asp Thr Leu Ser Thr Arg Cys Asn
                245                 250                 255

Glu Val Ser Ser Leu Trp Ala Pro Cys Leu Cys Asn Leu Glu Thr Cys
            260                 265                 270

Ile Gly Trp Val Pro Cys Gly Leu Lys Val Cys Lys Gly Lys Gly Val
        275                 280                 285

Ala Gly Ala Asp Ser Ser Gly Ala Gln Gln Ala Gln Pro Thr Asn
    290                 295                 300

Val Arg Cys Gly Ile Lys Thr Cys Arg Lys Cys Thr Gln Phe Thr Tyr
305                 310                 315                 320

Val Val Arg Gln Lys Gln Gln Cys Leu Trp Asp Glu
                325                 330

<210> SEQ ID NO 8
```

<211> LENGTH: 2366
<212> TYPE: DNA
<213> ORGANISM: Homo sapiens

<400> SEQUENCE: 8

```
ccgcgaggtg cgcggtctct ttaaggcggg tcctggtggt ttctgtttcc tgaaggaagt      60
gacgggggt gggattgaat gaaaagtgca aaacacaggc tcgcagcgct ggagcccggg      120
gccgcggagc cgggccgggg cagcgccgtc tccgcctcgg ggccgccggg ggcgccctgc      180
tgagcgctac ccacgtgcgt ccgcgccacc tcgcgggcga ccccgcggcc aaggcccccg      240
gcggagcggc tccgggcgc cccgaactag cccccaactt tgggcgaagt ttgcctgcgc      300
ctctccccgc ccccacgcgg cgcgccgggg ccgcggacgg cagcggcccc cggggatgcg      360
ccttcccggg gtaccctgg cgcgccctgc gctgctgctg ctgctgccgc tgctcgcgcc      420
gctgctggga acgggtgcgc cggccgagct gcgggtccgc gtgcggctgc cggacggcca      480
ggtgaccgag gagagcctgc aggcggacag cgacgcggac agcatcagcc tcgagctgcg      540
caagcccgac ggcaccctcg tctccttcac cgccgacttc aagaaggatg tgaaggtctt      600
ccgggccctg atcctggggg agctggagaa ggggcagagt cagttccagg ccctctgctt      660
tgtcacccag ctgcagcaca atgagatcat ccccagtgag gccatggcca agctccggca      720
gaaaaatccc cgggcagtgc ggcaggcgga ggaggttcgg ggtctggagc atctgcacat      780
ggatgtcgct gtcaacttca gccaggggc cctgctgagc ccccatctcc acaacgtgtg      840
tgccgaggcc gtggatgcca tctacacccg ccaggaggat gtccggttct ggctggagca      900
aggtgtggac agttctgtgt tcgaggctct gcccaaggcc tcagagcagg cggagctgcc      960
tcgctgcagg caggtgggg accgcgggaa gccctgcgtc tgccactatg gcctgagcct     1020
ggcctggtac ccctgcatgc tcaagtactg ccacagccgc gaccggccca cgccctacaa     1080
gtgtggcatc cgcagctgcc agaagagcta cagcttcgac ttctacgtgc cccagaggca     1140
gctgtgtctc tgggatgagg atccctaccc aggctagggt gggagcaacc tgggcgggtg     1200
gctgctctgg gcccactgct cttccaccagc cactagaggg ggtggcaacc cccacctgag     1260
gccttatttc cctccctccc cactcccctg gccctagagc ctgggcccct ctggcccat     1320
ctcacatgac tgtgaagggg gtgtggcatg gcaggggc tcatgaaggc accccatc     1380
ccaccctgtg ccttccttgc gggcagagag ggagagaagg gctccccaga tctacacccc     1440
tccctcctgc atctcccctg gagtgttcac ttgcaagctg ccaaaacatg atggcctctg     1500
gttgttctgt tgaactcctt gaacgtttag accctaaaag gagtctatac ctggacaccc     1560
acctccccag acacaactcc cttccccatg cacacatctg gaaggagctg gcccctcagt     1620
cccttcctac tccccaacaa ggggctcact atccccaaag aaggagctgt tggggaccca     1680
cgacgcagcc cctgtactgg attacagcat attctcatct ctggccccga ggctgcctgt     1740
ggggcgagtg gagacctccc atcactgaga cagatcacag accacgagtg cctttcccgg     1800
acctggacgt tgcctccaaa acaggcacca gctctttccc tctctagaca gaaatatttt     1860
tgtaaggttc tgggggcaggg agggagcatg aagtacgagg aaaacttgaa ttccagattt     1920
ttaatgcaaa gtatttatca tttctaccag aaataaacgt tttaagtttt tacttgacta     1980
atgagaccca gagtttggag aaaacttttg gccaatgctg ccacctgatg tcagaaagtg     2040
tccccacacc ctagcagtgg cctatcttgg aacaagaact tcgaaagcac ctactgtgtg     2100
```

-continued

```
ctcagccatt tgaggaagga aggaggagaa ggaagatgtt actagggaag gatgagataa    2160
aacttctgca cccaagacaa tgagacagac ataactgcaa ccgtagtaag ccagtcagaa    2220
atagccagcg cgaaggcaag agatggggtg gagattggaa ccccgcttca gatctgggct    2280
cggctactta cctgctgtgc agccatgggt caagttgctt gacctctctg tgcctccact    2340
cccttagcta taaaatgagc ttactt                                         2366
```

```
<210> SEQ ID NO 9
<211> LENGTH: 270
<212> TYPE: PRT
<213> ORGANISM: Homo sapiens

<400> SEQUENCE: 9
```

Arg Leu Pro Gly Val Pro Leu Ala Arg Pro Ala Leu Leu Leu Leu Leu
 1               5                   10                  15

Pro Leu Leu Ala Pro Leu Leu Gly Thr Gly Ala Pro Ala Glu Leu Arg
            20                  25                  30

Val Arg Val Arg Leu Pro Asp Gly Gln Val Thr Glu Glu Ser Leu Gln
        35                  40                  45

Ala Asp Ser Asp Ala Asp Ser Ile Ser Leu Glu Leu Arg Lys Pro Asp
    50                  55                  60

Gly Thr Leu Val Ser Phe Thr Ala Asp Phe Lys Lys Asp Val Lys Val
65                  70                  75                  80

Phe Arg Ala Leu Ile Leu Gly Glu Leu Glu Lys Gly Gln Ser Gln Phe
                85                  90                  95

Gln Ala Leu Cys Phe Val Thr Gln Leu Gln His Asn Glu Ile Ile Pro
            100                 105                 110

Ser Glu Ala Met Ala Lys Leu Arg Gln Lys Asn Pro Arg Ala Val Arg
        115                 120                 125

Gln Ala Glu Glu Val Arg Gly Leu Glu His Leu His Met Asp Val Ala
    130                 135                 140

Val Asn Phe Ser Gln Gly Ala Leu Leu Ser Pro His Leu His Asn Val
145                 150                 155                 160

Cys Ala Glu Ala Val Asp Ala Ile Tyr Thr Arg Gln Glu Asp Val Arg
                165                 170                 175

Phe Trp Leu Glu Gln Gly Val Asp Ser Ser Val Phe Glu Ala Leu Pro
            180                 185                 190

Lys Ala Ser Glu Gln Ala Glu Leu Pro Arg Cys Arg Gln Val Gly Asp
        195                 200                 205

Arg Gly Lys Pro Cys Val Cys His Tyr Gly Leu Ser Leu Ala Trp Tyr
    210                 215                 220

Pro Cys Met Leu Lys Tyr Cys His Ser Arg Asp Arg Pro Thr Pro Tyr
225                 230                 235                 240

Lys Cys Gly Ile Arg Ser Cys Gln Lys Ser Tyr Ser Phe Asp Phe Tyr
                245                 250                 255

Val Pro Gln Arg Gln Leu Cys Leu Trp Asp Glu Asp Pro Tyr
            260                 265                 270

```
<210> SEQ ID NO 10
<211> LENGTH: 10
<212> TYPE: PRT
<213> ORGANISM: Artificial Sequence
```

```
-continued

<220> FEATURE:
<223> OTHER INFORMATION: Predicted protease cleavage site of SEQ ID NO:
      3

<400> SEQUENCE: 10

Ala Pro Leu Leu Gly Thr Gly Ala Pro Ala
1               5                   10
```